United States Patent
Fields et al.

(10) Patent No.: US 11,337,790 B2
(45) Date of Patent: May 24, 2022

(54) SYSTEMS AND METHODS FOR PROTECTING THE CEREBRAL VASCULATURE

(71) Applicant: Claret Medical, Inc., Santa Rosa, CA (US)

(72) Inventors: Antony J. Fields, San Francisco, CA (US); Cameron Paul Purcell, Santa Rosa, CA (US); Daniel Wayne Fifer, Windsor, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 274 days.

(21) Appl. No.: 15/901,819

(22) Filed: Feb. 21, 2018

(65) Prior Publication Data

US 2018/0235742 A1   Aug. 23, 2018

Related U.S. Application Data

(60) Provisional application No. 62/462,150, filed on Feb. 22, 2017.

(51) Int. Cl.
*A61F 2/01*   (2006.01)
*A61M 25/01*   (2006.01)

(52) U.S. Cl.
CPC ............ *A61F 2/012* (2020.05); *A61F 2/0105* (2020.05); *A61F 2/011* (2020.05); *A61F 2002/016* (2013.01); *A61F 2002/018* (2013.01); *A61F 2230/0093* (2013.01); *A61M 25/0147* (2013.01)

(58) Field of Classification Search
CPC ...... A61F 2/01; A61F 2/013; A61F 2002/011; A61F 2002/016; A61F 2002/018
See application file for complete search history.

(56) References Cited

U.S. PATENT DOCUMENTS

| 3,472,230 A | 10/1969 | Fogarty |
| 4,619,246 A | 10/1986 | Molgaard-Nielsen et al. |
| 4,630,609 A | 12/1986 | Chin |

(Continued)

FOREIGN PATENT DOCUMENTS

| DE | 10049812 | 4/2002 |
| EP | 1400257 A2 | 3/2004 |

(Continued)

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).

(Continued)

*Primary Examiner* — Todd J Scherbel
(74) *Attorney, Agent, or Firm* — Seager, Tufte & Wickhem LLP

(57) ABSTRACT

Vascular filters and deflectors and methods for filtering bodily fluids. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

20 Claims, 38 Drawing Sheets

(56) References Cited

U.S. PATENT DOCUMENTS

| | | |
|---|---|---|
| 4,650,466 A | 3/1987 | Luther |
| 4,706,671 A | 11/1987 | Weinrib |
| 4,723,549 A | 2/1988 | Wholey |
| 4,873,978 A | 10/1989 | Ginsburg |
| 5,108,419 A | 4/1992 | Reger |
| 5,192,286 A | 3/1993 | Phan |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,814,064 A | 9/1998 | Daniel |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya et al. |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika |
| 6,336,934 B1 | 1/2002 | Gilson et al. |
| 6,346,116 B1 | 2/2002 | Brooks et al. |
| 6,361,545 B1 | 3/2002 | Macoviak et al. |
| 6,364,900 B1 | 4/2002 | Heuser |
| 6,371,970 B1 | 4/2002 | Khosravi et al. |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson et al. |
| 6,440,120 B1 | 8/2002 | Maahs |
| 6,454,799 B1 | 11/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,922,732 B2 | 3/2011 | Mazzocchi et al. |
| 7,918,859 B2 | 4/2011 | Katoh et al. |
| 7,976,562 B2 | 7/2011 | Bressler et al. |
| 7,998,104 B2 | 8/2011 | Chang |
| 8,002,790 B2 | 8/2011 | Brady et al. |
| 8,021,351 B2 | 9/2011 | Boldenow et al. |
| 8,052,713 B2 | 11/2011 | Khosravi et al. |
| 8,092,483 B2 | 1/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 | 2/2017 | Purcell et al. |
| 9,636,205 B2 | 5/2017 | Lee et al. |

(56) References Cited

U.S. PATENT DOCUMENTS

| | | |
|---|---|---|
| 9,943,395 B2 | 4/2018 | Fifer et al. |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 7/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0211095 A1 | 8/2010 | Carpenter |
| 2010/0228280 A1 | 9/2010 | Groothuis et al. |
| 2010/0312268 A1 | 12/2010 | Belson |
| 2010/0324589 A1 | 12/2010 | Carpenter et al. |
| 2011/0022076 A1 | 1/2011 | Lashinski |
| 2011/0066221 A1 | 3/2011 | White et al. |
| 2012/0046739 A1 | 2/2012 | von Oepen et al. |
| 2012/0095500 A1 | 4/2012 | Heuser |
| 2012/0172916 A1 | 7/2012 | Fifer et al. |
| 2012/0172920 A1* | 7/2012 | Fifer ............... A61F 2/013 606/200 |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0282379 A1 | 9/2014 | Lee et al. |
| 2015/0039016 A1 | 2/2015 | Naor et al. |
| 2015/0209131 A1 | 7/2015 | Fifer et al. |
| 2015/0230910 A1 | 8/2015 | Lashinski et al. |
| 2015/0335416 A1 | 11/2015 | Fifer et al. |
| 2016/0058541 A1 | 3/2016 | Schotzko et al. |
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |
| 2017/0112609 A1 | 4/2017 | Purcell et al. |
| 2017/0181834 A1 | 6/2017 | Fifer et al. |
| 2017/0202657 A1 | 7/2017 | Lee et al. |

FOREIGN PATENT DOCUMENTS

| | | |
|---|---|---|
| EP | 1253871 | 2/2007 |
| EP | 2303384 | 4/2011 |
| EP | 2391303 | 12/2011 |
| EP | 2480165 | 8/2012 |
| EP | 2658476 | 11/2013 |
| EP | 2387427 | 8/2014 |
| JP | 2003-505216 | 2/2003 |
| JP | 2003-526451 | 9/2003 |
| JP | 2003-290231 | 10/2003 |
| JP | 3535098 B2 | 6/2004 |
| JP | 2006-500187 | 1/2006 |
| JP | 2008-511401 | 4/2008 |
| JP | 2008-515463 | 5/2008 |
| JP | 2011-525405 A | 9/2011 |
| WO | WO 99/23976 | 5/1999 |
| WO | WO 01/67989 | 9/2001 |
| WO | WO 2004/026175 | 4/2004 |
| WO | WO 2005/118050 | 12/2005 |
| WO | WO 2006/026371 | 3/2006 |
| WO | WO 2008/033845 | 3/2008 |

(56) References Cited

FOREIGN PATENT DOCUMENTS

| | | |
|---|---|---|
| WO | WO 2008/100790 | 8/2008 |
| WO | WO 2008/113857 | 9/2008 |
| WO | WO 2009/032834 | 3/2009 |
| WO | WO 2010/008451 | 1/2010 |
| WO | WO 2010/081025 | 7/2010 |
| WO | WO 2010/083527 A2 | 7/2010 |
| WO | WO 2010/088520 A2 | 8/2010 |
| WO | WO 2011/034718 A2 | 3/2011 |
| WO | WO 2011/017103 A2 | 10/2011 |
| WO | WO 2012/092377 A1 | 7/2012 |

OTHER PUBLICATIONS

Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).

Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

* cited by examiner

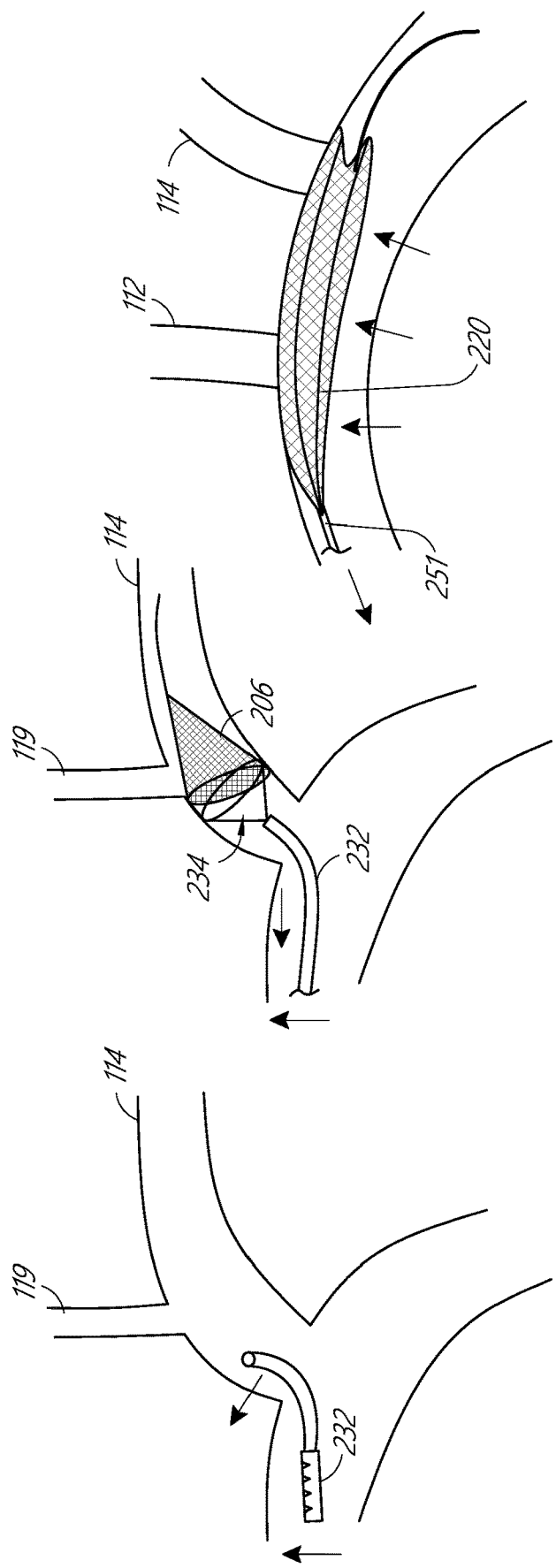

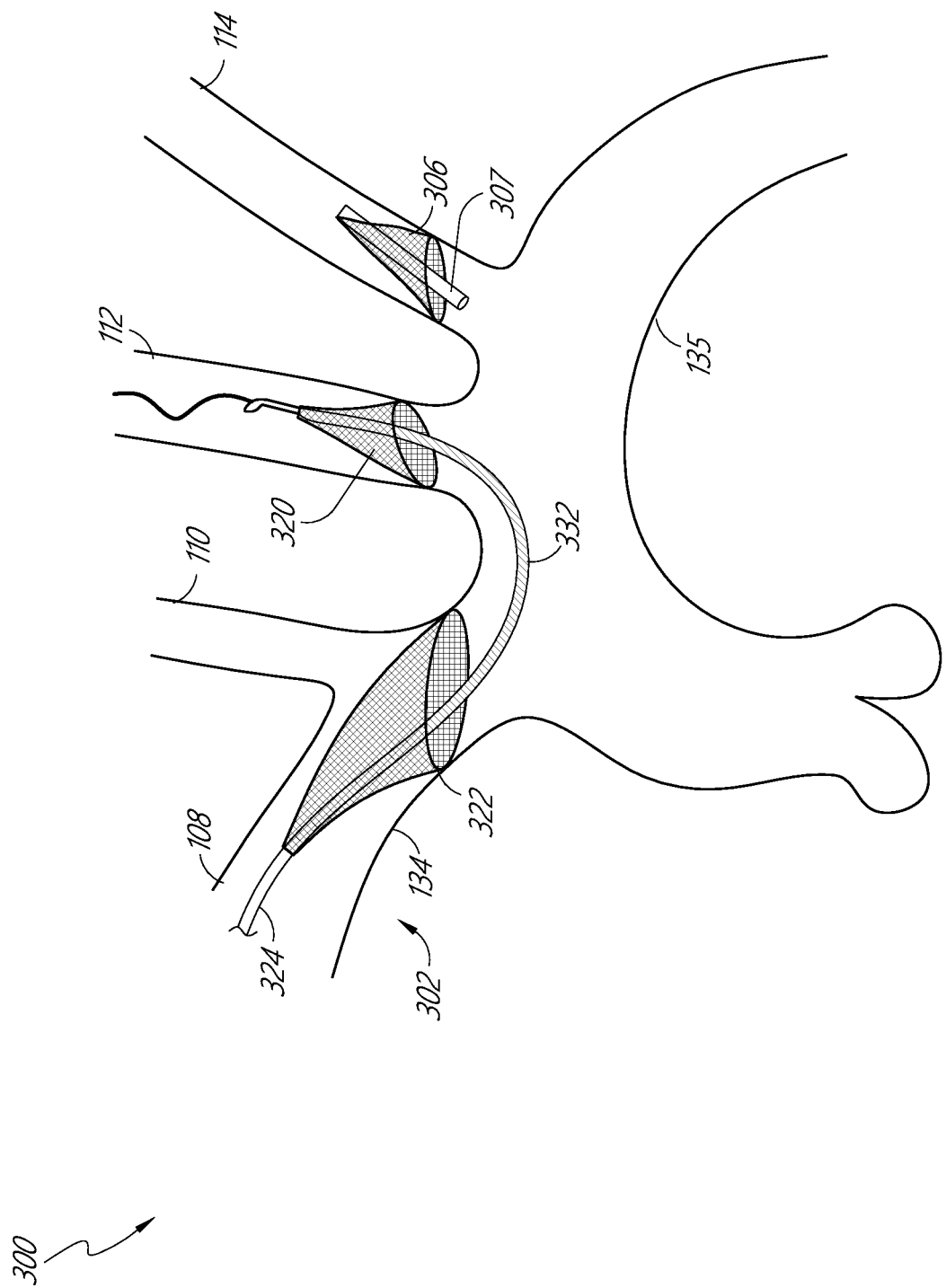

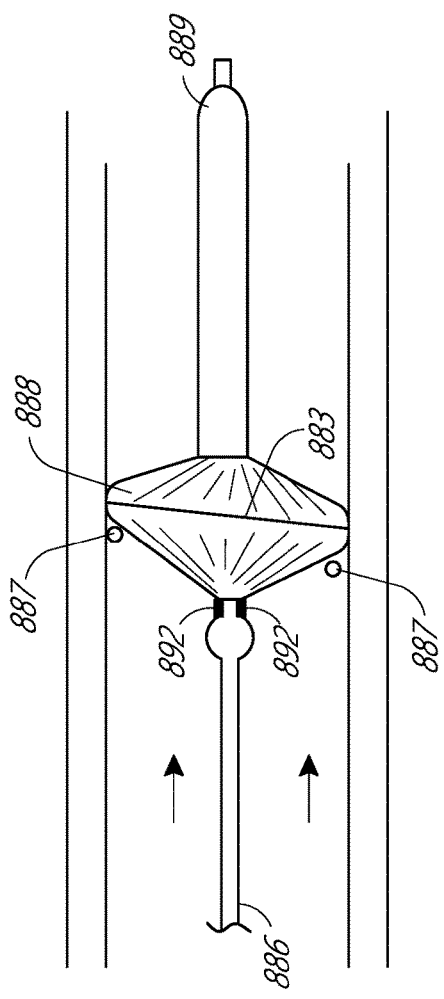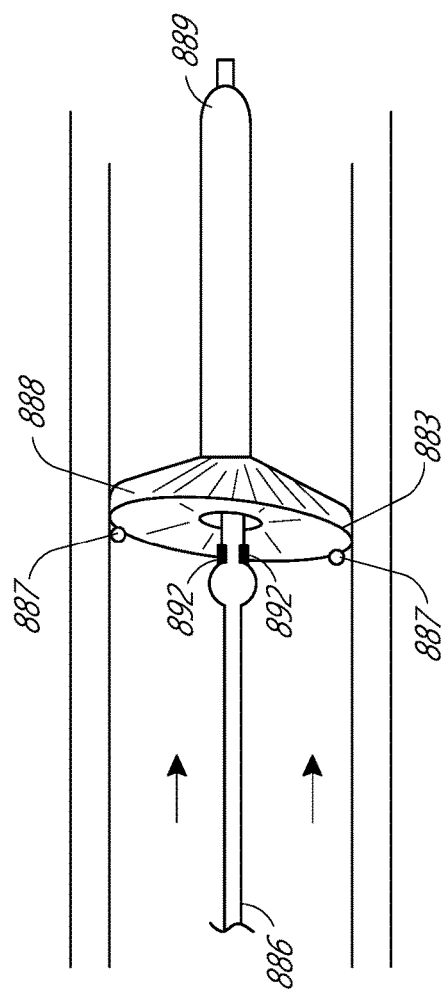
FIG. 8E
FIG. 8F

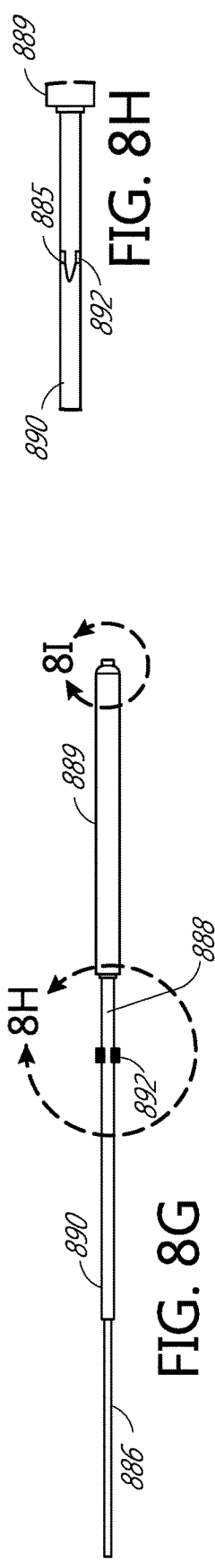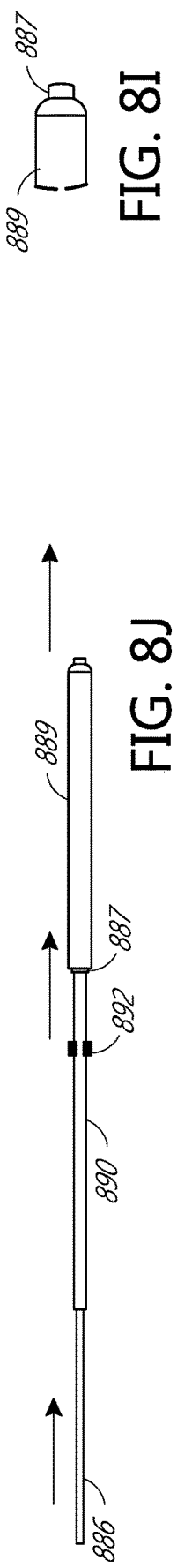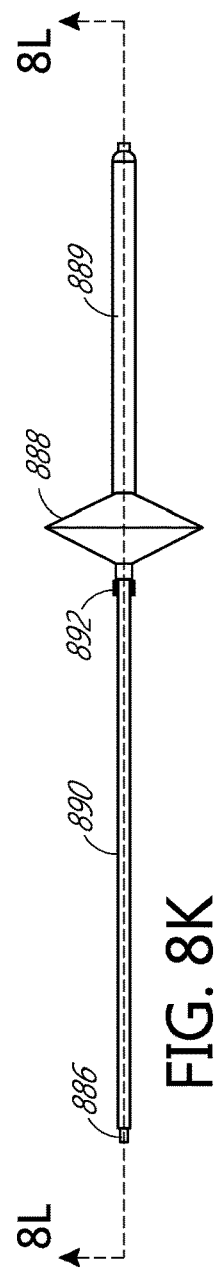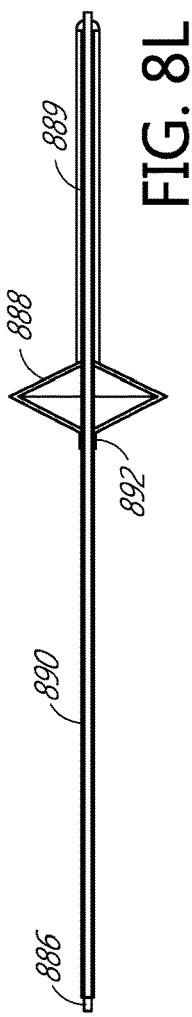

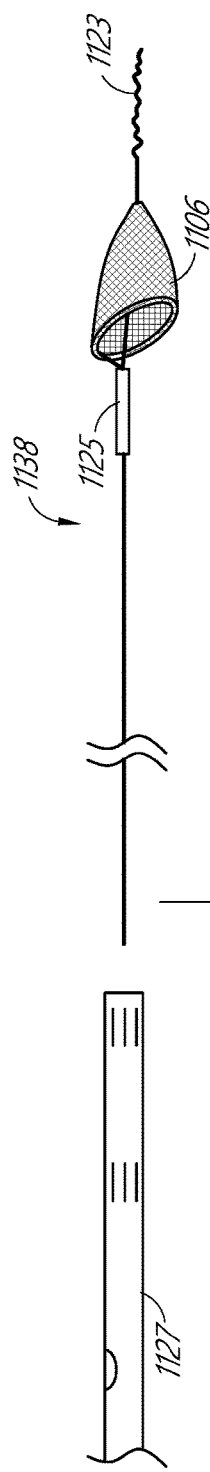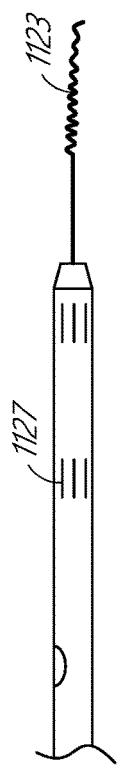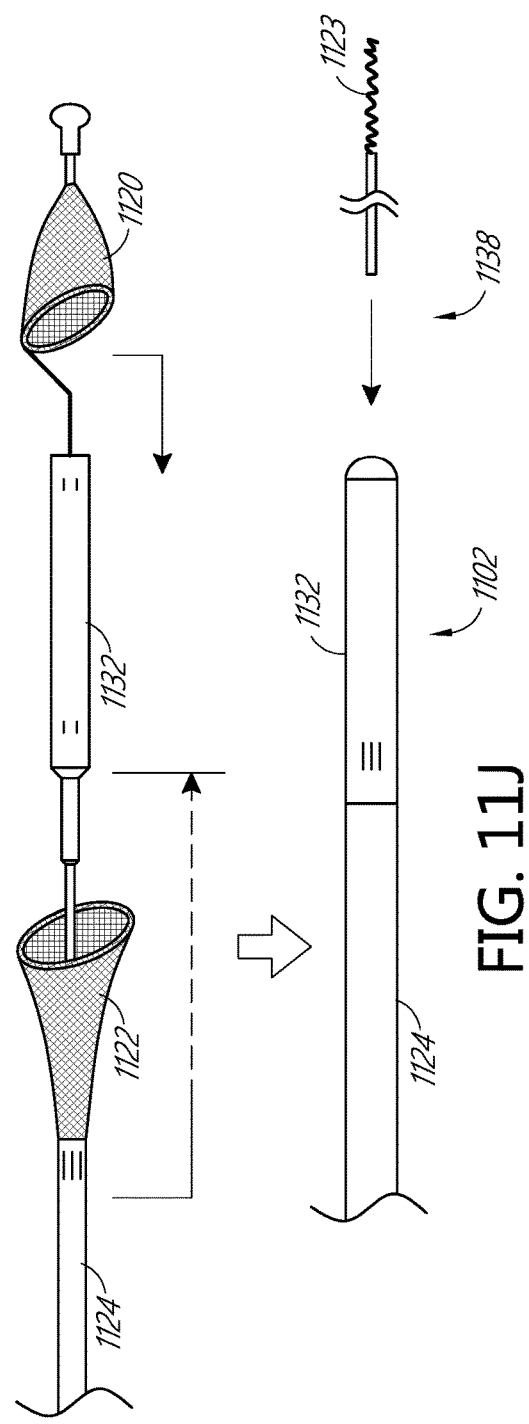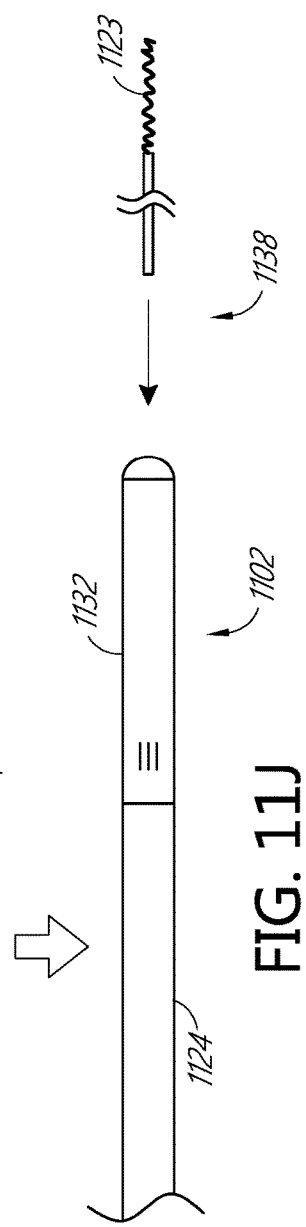
FIG. 11G
FIG. 11H
FIG. 11I
FIG. 11J

SYSTEMS AND METHODS FOR PROTECTING THE CEREBRAL VASCULATURE

INCORPORATION BY REFERENCE TO ANY PRIORITY APPLICATIONS

This application claims the priority benefit under 35 U.S.C. § 119(e) of U.S. Provisional Application No. 62/462,150, filed Feb. 22, 2017; the entire contents of which are hereby incorporated by reference and should be considered a part of this specification.

Any and all applications for which a foreign or domestic priority claim is identified in the Application Data Sheet as filed with the present application are hereby incorporated by reference under 37 C.F.R. § 1.57.

BACKGROUND

Field

The disclosure relates to devices and methods for filtering body fluids such as blood and/or selectively deflecting potentially embolic particles from the body fluid. The devices can be catheter-based for insertion into a vascular system of a subject.

Description of the Related Art

There are four arteries that carry oxygenated blood to the brain, i.e., the right and left vertebral arteries, and the right and left common carotid arteries. Various procedures conducted on the human body, e.g., TAVR, aortic valve valvuloplasty, carotid artery stenting, closure of the left atrial appendage, mitral valve annuloplasty, mitral valve replacement, mitral valve repair, TEVAR, etc. can cause and/or dislodge native or foreign materials, which dislodged bodies can travel into one or more of the cerebral arteries resulting in, inter alia, stroke. Therefore, filtering the innominate artery, right subclavian artery, right brachiocephalic artery, right common carotid artery, left vertebral artery, and left subclavian artery at aortic branch arches or at the arches of said arteries may be useful to prevent dislodged materials from migrating to the cerebral area.

Thromboembolic disorders, such as stroke, pulmonary embolism, peripheral thrombosis, atherosclerosis, and the like affect many people. These disorders are a major cause of morbidity and mortality in the United States and throughout the world. Thromboembolic events are characterized by an occlusion of a blood vessel. The occlusion can be caused by a clot, which is viscoelastic or jelly-like and comprises platelets, fibrinogen, and other clotting proteins Percutaneous aortic valve replacement procedures have become popular, but stroke rates related to this procedure are between two and twenty percent. During catheter delivery and valve implantation, plaque, calcium or other material may be dislodged from the vasculature and may travel through the carotid circulation and into the brain. When an artery is occluded by a clot or other embolic material, tissue ischemia develops from a lack of oxygen and nutrients. The ischemia progresses to tissue infarction or cell death if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Reestablishing blood flow and removal of the thrombus is highly desirable. Surgical techniques and medicaments to remove or dissolve obstructing material have been developed, but exposing a subject to surgery may be traumatic and is best avoided when possible. Additionally, the use of certain devices carry risks such as the risk of dislodging foreign bodies, damaging the interior lining of the vessel as the catheter is being manipulated, blood thinning, etc.

SUMMARY

The present disclosure and its various embodiments can provide compound systems of filters and/or deflectors for collecting and/or deflecting debris in a manner such that all four cerebral arteries are protected. Embodiments of the present disclosure addresses debris, tissue, or the like, that can be dislodged during an endovascular procedure, travel into the cerebral vasculature, and embolize, leading to stroke or ischemia in an artery occluded, partially or totally, by the clot. For example, during a transcatheter aortic valve replacement (TAVR), stenotic material around the valve can be dislodged during implantation of the artificial valve. Moreover, atheromas and calcium along and within the aorta and aortic arch can be dislodged as the TAVR catheter is advanced toward the diseased aortic valve and subsequently withdrawn after implantation is completed. In addition, pieces of the catheter itself can be stripped away during delivery and implantation. These various forms of vascular debris, whether native or foreign, can then travel into one or more cerebral arteries, embolize, and cause a stroke or strokes.

Embodiments of the present disclosure are intended to address these potentially devastating cerebral events by providing a delivery system comprised of filters and/or deflectors and/or a combinations thereof, to intercept this debris before it can enter any of the cerebral arteries.

For example, certain aspects of the disclosure are directed toward a method of preventing embolic material from entering the cerebral vasculature. The method can include introducing a protection system into an aortic arch. The protection system can include an outer sheath, a distal filter portion, and a deflector portion having a first lobe and a second lobe. The method can also include deploying the distal filter portion in a first vessel and deploying the deflector portion in the aortic arch such that the first lobe prevents debris from flowing into a second vessel and the second lobe prevents debris from flowing into a third vessel. After deploying the distal filter portion and the deflector portion, the distal filter portion is distal to the deflector portion.

A protection system for use with the above-described method can include an outer sheath, an articulating distal sheath positioned radially inward of the outer sheath, a filter wire positioned radially inward of the articulating distal sheath, a distal filter portion carried by the filter wire, and a deflector portion positioned radially between the outer sheath and the articulating distal sheath in a pre-deployment configuration. The deflector portion can include a first lobe configured to seal against an ostium of a second vessel and a second lobe configured to seal against an ostium of a third vessel. In a post-deployment configuration, the distal filter portion is positioned distal to the deflector portion.

Another method of preventing embolic material from entering the cerebral vasculature can include introducing a protection system into an aortic arch. The protection system can include an articulating distal sheath, a first or proximal filter, a second or secondary distal filter connected to the first filter by a first linking or tethering portion, and a third or distal filter connected to the second filter by a second linking or tethering portion. Each of the first filter, the second filter, and the third filter can be configured to be deployed from the articulating distal sheath. The method can also include deploying the first filter in a first vessel, then deploying the second filter in a second vessel, and then deploying the third filter in a third vessel.

A protection system for use with the above-described method can include an articulating distal sheath, a first or proximal filter, a second or secondary distal filter connected to the first filter by a first linking or tethering portion; and a third or distal filter connected to the second filter by a second linking or tethering portion. Each of the first filter, the second filter, and the third filter can be configured to be deployed from the articulating distal sheath. The first tethering portion can be sufficiently flexible to extend from the first vessel to the second vessel. The second tethering portion can be sufficient flexible to extend from the second vessel to the third vessel.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 2F-2H show different example methods of conforming the deflector to the vessel wall.

FIGS. 3A-3B show another example of a protection system in which two filters are serially loaded into the articulating distal sheath of the first filter assembly and the distal filter is detachable.

FIGS. 8E-8L show another example of a filter design that can be used with any protection system described herein.

DETAILED DESCRIPTION

Overview

The disclosure generally relates to devices and methods for filtering fluids and/or deflecting debris contained within fluids, including body fluids such as blood. A filtering or deflecting device can be positioned in an artery before and/or during an endovascular procedure, for example transcatheter aortic valve implantation (TAVI) or replacement (TAVR), transcatheter mitral valve implantation or repair (TMVR), surgical aortic valve replacement (SAVR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc., to inhibit or prevent embolic material such as debris, emboli, thrombi, etc. resulting from entering the cerebral vasculature.

The devices may be used to trap particles in other blood vessels within a subject, and they can also be used outside of the vasculature. The devices described herein are generally adapted to be delivered percutaneously to a target location within a subject, but can be delivered in any suitable way and need not be limited to minimally-invasive procedures.

Figure 1:
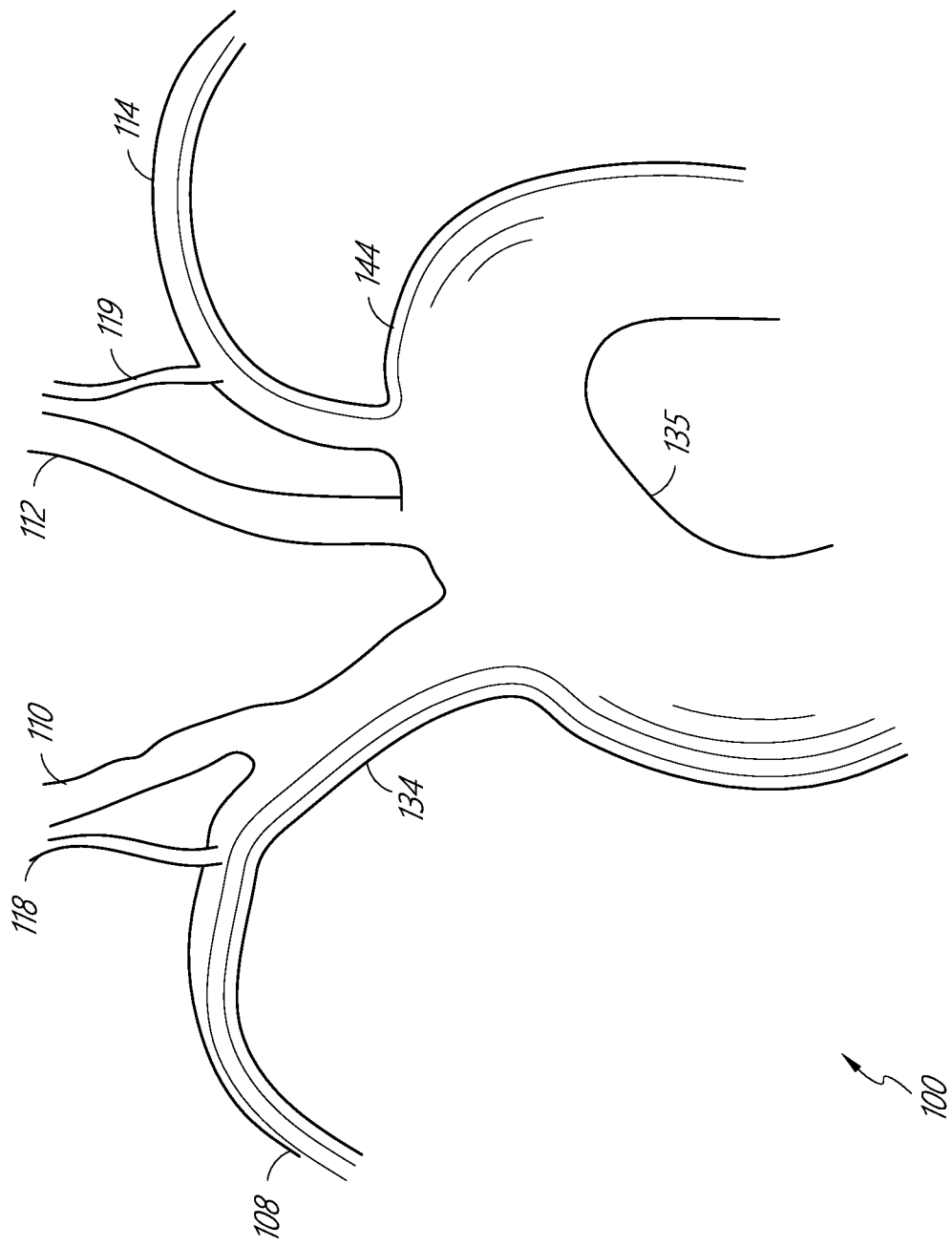
FIG. 1 shows the anatomy of the aortic branch.

FIG. 1 is a schematic perspective view of an aortic arch 135. The aortic arch 135 is upstream of the left and right coronary arteries (both not shown). The aortic arch 135 typically includes three great branch arteries: the brachiocephalic artery or innominate artery 134, the left common carotid artery 112, and the left subclavian artery 114. The innominate artery 134 branches to the right common carotid artery 110, then the right vertebral artery 118, and thereafter is the right subclavian artery 108. The right subclavian artery 108 supplies blood to, and may be directly accessed from (termed right radial access), the right arm. The left subclavian artery 114 branches to the left vertebral artery 119, usually in the shoulder area. The left subclavian artery 114 supplies blood to, and may be directly accessed from (termed left radial access), the left arm. The aortic arch 135 may be reached from the femoral artery (not shown).

Devices and methods, some of which are compatible and/or synergistic with the devices and methods described herein, have been developed to filter blood flowing to the innominate artery 134 and the left common carotid artery 112, which provide about 90% of the blood entering the cerebral vasculature. Examples are provided in U.S. Pat. No. 9,492,264, which is incorporated herein by reference in its entirety, and most particularly with respect to disclosure directed to devices and methods for protecting aortic arch branch arteries and structures of filter devices. Certain such devices and methods leave the left subclavian artery 114, and thus the left vertebral artery 119, which provides about 10% of the blood entering the cerebral vasculature, exposed to potential embolic material.

It may be preferred to achieve protection of all cerebral vessels from one access point. The present application discloses several single-access multi-vessel embodiments that can provide full cerebral protection with minimal arch interference.

Figure 2:
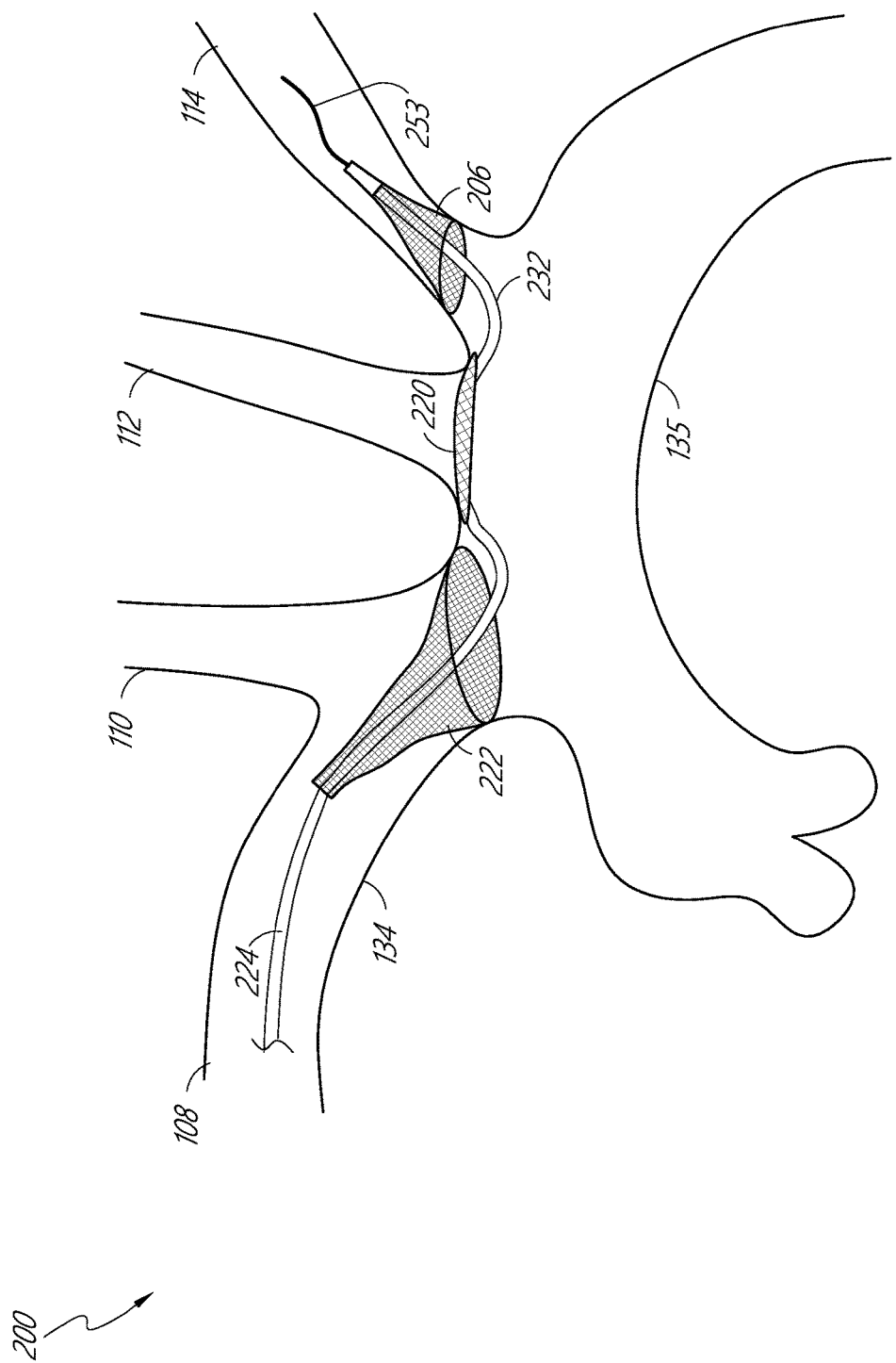
FIG. 2 shows an example protection system that uses a deflector to block the left common carotid artery.

FIG. 2 illustrates an example of a protection system 200 that can be inserted through a single access point from the right radial or brachial artery. The outer catheter 224 may have a diameter no greater than about 7 F (0.09 inches) or no greater than about 6 F (0.08 inches). The smaller diameter reduces possible complications associated with advancing the filter assembly through the vasculature.

The protection system 200 can include a proximal filter 222, a distal filter 206, and a deflector 220 configured to be deployed therebetween. The proximal filter 222 can be deployed in the brachiocephalic trunk 134. The left subclavian artery 114 can be cannulated with an independently steerable and positionable (e.g., rotatable and/or translatable) articulating distal sheath 232. A guidewire 253 can be utilized to facilitate positioning, and to interrogate (e.g., visualize and assist in positioning) the vessel during cannulation. A distal filter 206 can be deployed, e.g., by advancing the distal filter 206 or withdrawing the articulating distal sheath 232, in the left subclavian artery 114. The mechanisms for deploying the distal filter 206 and the proximal filter 222 can include features of the devices described in U.S. Pat. No. 9,492,264, which has been incorporated by reference herein. As shown in FIG. 2, the articulating distal sheath 232 can include a deflector 220 that can protect the ostium of the left common carotid artery 112. The deflector 220 can be mounted on or contained in the articulating distal sheath 232, or the deflector 220 can be separately deployable from the articulating distal sheath 232. Removal of the device can be accomplished as a reversal of the deployment steps into the outer catheter 124.

The filters 222, 206 and the deflector 220 may be deployed in any order. In a modified method, the device 200 can be introduced into the left radial or brachial artery. A first filter 222 can be deployed in the left subclavian artery 114 between the left vertebral branch 119 and the ostium of the aortic arch 135. A second filter 206 can be deployed in the brachiocephalic trunk 134, and a deflector 220 can be deployed to cover the ostium of the left common carotid artery 112.

Figure 2A:
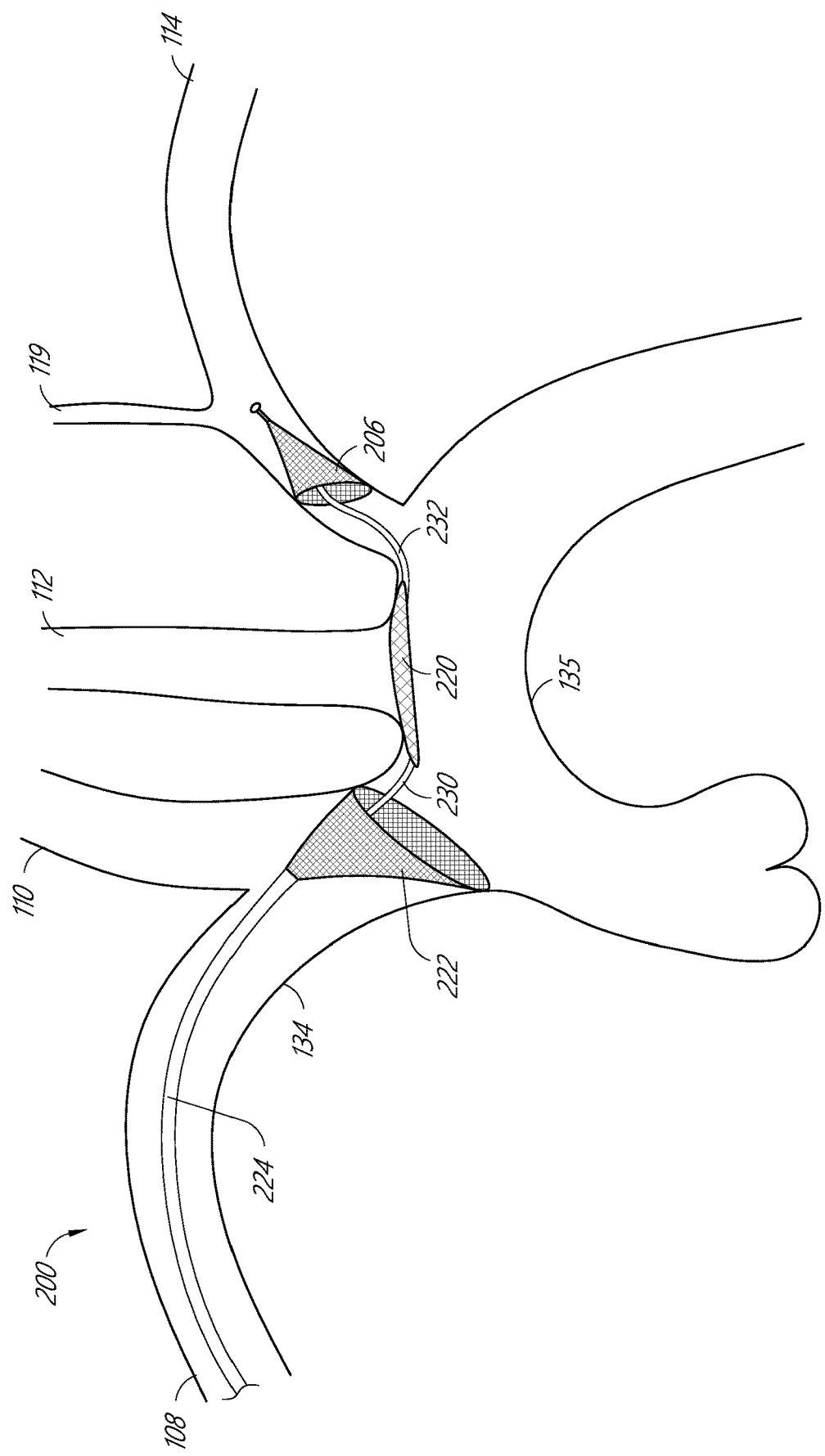
FIG. 2A shows another example protection system that uses a knuckle to orient the deflector to block the left common carotid artery.

As shown in FIG. 2A, a protection system 200 can be used to protect all three vessels. A distal filter 220 can be configured to protect the left subclavian 114, the proximal filter 222 can be left in the brachiocephalic artery 134, and in certain arrangements, a deflector 220 can be added between the distal 206 and proximal filter 222 to protect the left common carotid artery 112. The mechanisms for deploying the proximal filter 222 and the distal filter 206 can include any features of the filter systems described in U.S. Pat. No. 9,492,264, which is incorporated by reference herein. Unlike the protection system 200 shown in FIG. 2, the protection system can include a knuckle 230 located between the deflector 220 and the proximal filter 222. The knuckle 230 is movable, maneuverable, or otherwise steerable, which can help create a tight bend to properly support and position the deflector 220.

In one arrangement, the proximal filter 222 can be the largest filter and deployed in the proximal location when approaching from the right radial artery. This can be followed by deployment of the deflector 220 and the distal filter 206 distal of the proximal filter 222. The mechanisms to deploy the filters, to deflect the articulating sheath for cannulation, and to additionally deploy the deflector can utilize any of the mechanisms described in U.S. Pat. No. 9,492,264, which is incorporated by reference herein. In other methods, the deflector 220 and/or the distal filter 206 may be deployed prior to the proximal filter 222.

Figure 2B:
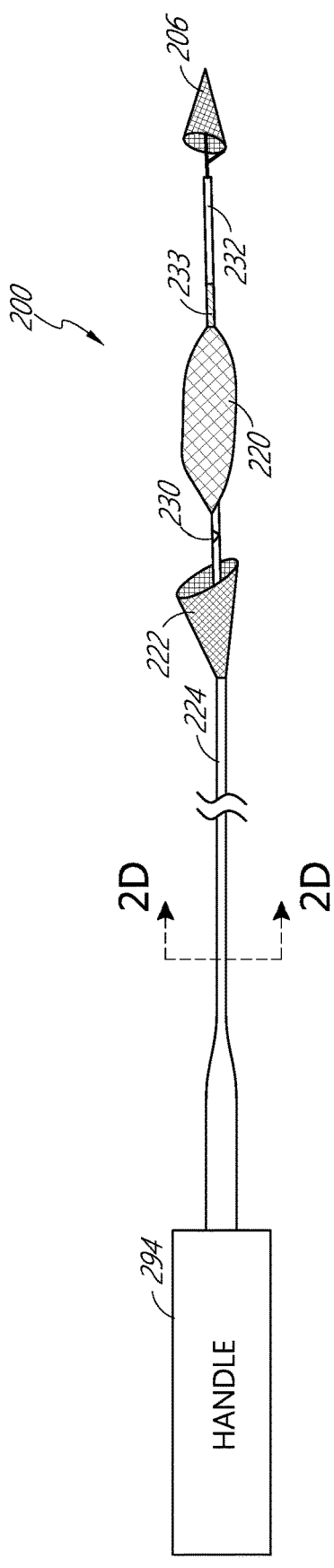
FIGS. 2B-2C show the example protection system of FIG. 2A with the articulating distal sheath deflecting from a first configuration (FIG. 2B) to a second configuration (FIG. 2C).
Figure 2C:
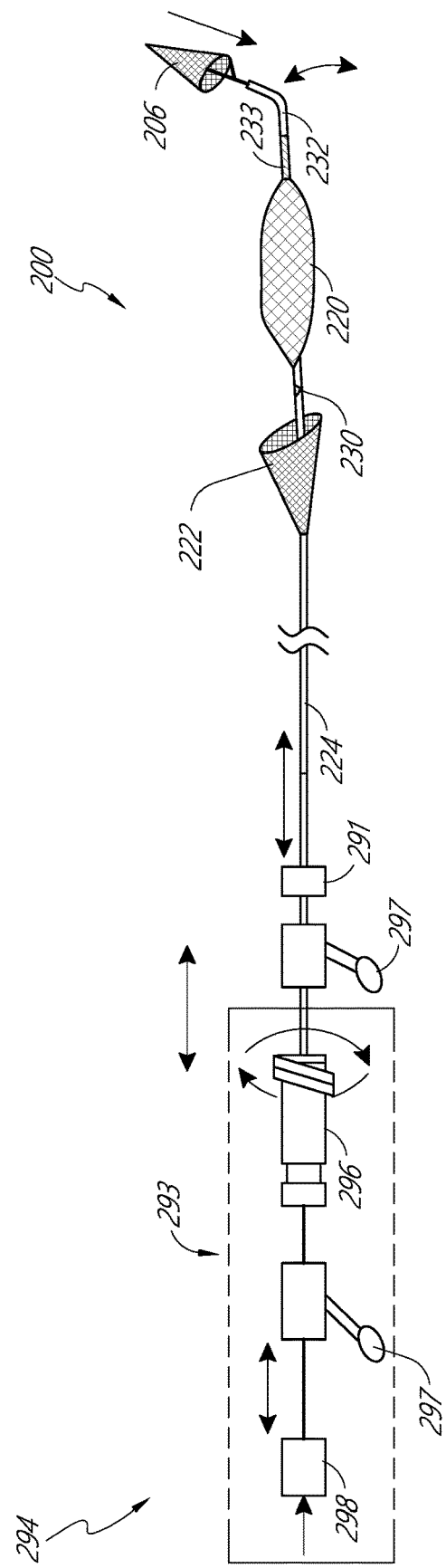
Figure 2D:
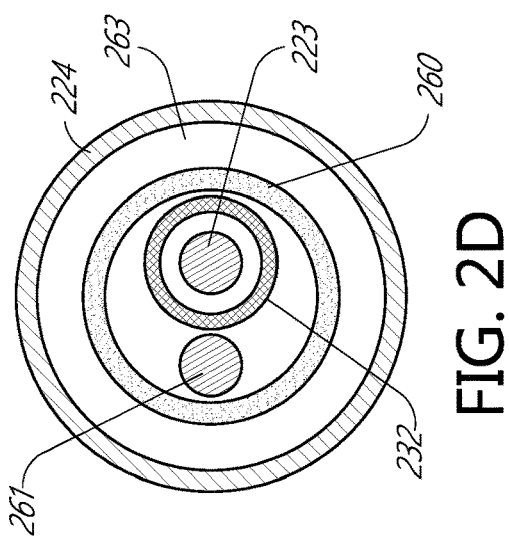
FIG. 2D shows a cross-section of FIG. 2B taken through line 2D-2D.

FIGS. 2B-2D illustrate the various components of the protection system 200 shown in FIG. 2A. As shown in FIG. 2B-2C, the protection system 200 can optionally include a skeleton portion 233. The length between the knuckle 230 and the skeleton portion 233 of the articulating distal sheath 232 can be adjusted using one or more pull-wires. The knuckle 230 and the skeleton portion 233 can be two separate components that move relative to each other or part of a single component sufficiently flexible to bend when pulled toward each other. For example, a distal end of one pull wire can be connected to the knuckle 230 and a distal end of another pull wire can be connected to the skeleton portion 233. The region between the knuckle 230 and the skeleton portion 233 can be foreshortened to properly position the deflector 220 against the vessel wall. The skeleton portion 233 can be a laser cut, thin-walled tube that is designed to bend before any other portion of the articulating distal sheath 232.

Each end of the deflector 220 may be mounted to the articulating distal sheath 232 such that the deflector 220 is free to deflect. The deflector 220 can be rotated, translated, and/or apposed to the roof of the aortic arch 135 by pulling against either the deflected articulating distal sheath 232 or the deployed distal filter 206. FIG. 2D shows a cross section of the device through line 2D-2D in FIG. 2B that shows the device 200 can include an outer sheath 224, a core shaft 260 supporting the proximal filter 222 and positioned radially inward of the outer sheath 224, a pull wire 261 for controlling the articulating distal sheath 232, an inner member 232 supporting the distal filter 206, and/or a guidewire 223 extending through the inner member 232. A lumen space 263 between the outer sheath 224 and the core shaft 260 can provide space for the proximal filter 222 and the deflector 220.

The handle 294 shown in FIGS. 2B-2C can include a distal filter actuator 298. For example, the distal filter actuator 298 can be advanced or withdrawn to control a position of the distal filter 206, as indicated by the arrows near the distal filter slider actuator 298 in FIG. 2C. Distal to the distal filter actuator 298, the handle 294 can include a port 297 for flushing fluids. Distal to the port 207, the handle 294 can include an actuation mechanism 296 for articulating the articulating distal sheath 232 (as shown by the arrows near actuation mechanism 296). The actuation mechanism 296 can include a screw drive mechanism to deflect the articulating distal sheath 232 by rotating the actuation mechanism 296. The screw drive mechanism can be self-locking to prevent unintentional deflection of the articulating distal sheath 232. The rear portion 293 (outlined in the dashed box) of the handle 294 can be translated to move the articulating distal sheath 232, deflector 220, and/or distal filter 206. Distal to the actuation mechanism 296, the handle 294 can include an additional flush port 297. Distal to the flush port 297, the handle 294 can include an actuation mechanism 291, for example a slider, to retract and advance the outer sheath 224 (as shown by the arrows near actuation mechanism 291), which releases and retrieves the proximal filter 222. Each of these actuation mechanisms 298, 296, 291 can be sequentially positioned along the handle 294 according to how the procedure is performed, but the actuation mechanisms 298, 296, 291 can take on different configurations or be positioned in a different order.

Figure 2E:
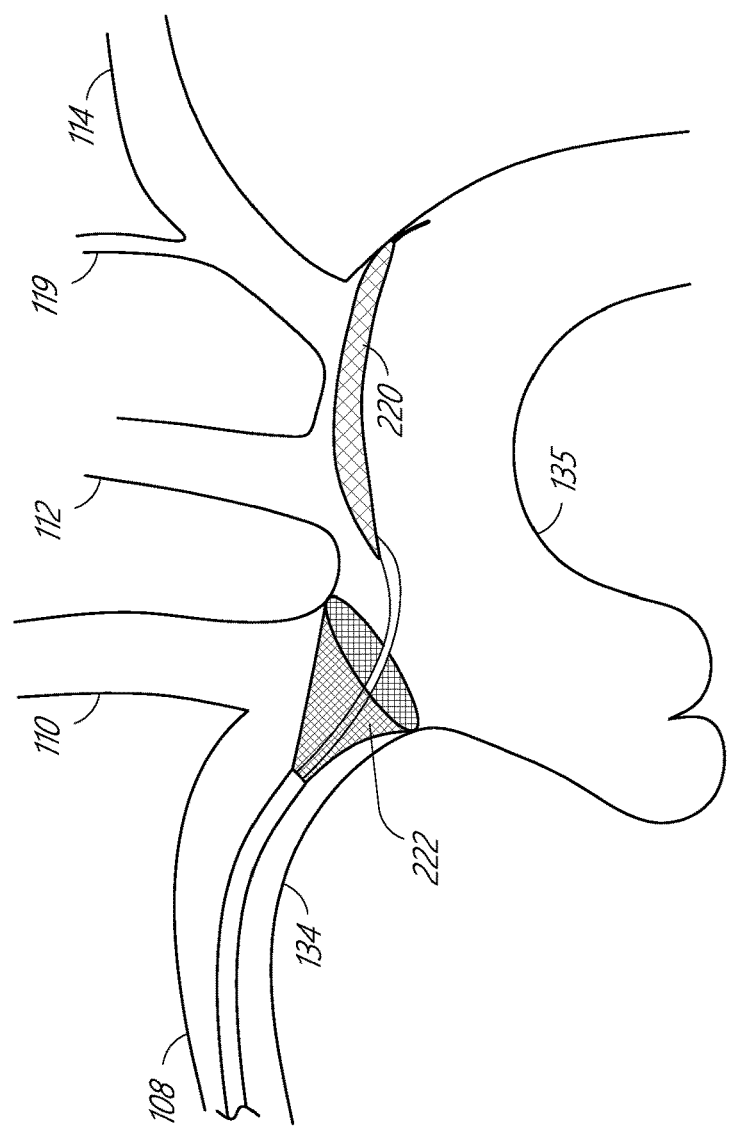
FIG. 2E shows an example of the difficulty associated with positioning a deflector against the vessel wall.

As shown FIG. 2E, a challenge with deflectors is apposing the deflector 220 against the target vessel and avoiding interference with the index procedure. In order to properly seal against the target vessel, a force can be provided to conform the deflector to the vessel wall. The deflectors can push off the wall opposite the target vessel location, compressing the deflector into place. However, this creates a risk of interfering with the other procedures.

An alternative is to conform the deflector by pulling it up with tension. For example, FIGS. 2F-2H illustrate three different methods of conforming the deflector 220 to the vessel wall. These methods can be used independently or in combination with each other. As shown in FIG. 2F, an articulating distal sheath 232 can be used to properly orient the deflector 220. With such an articulating sheath 232, the left subclavian 114 can be cannulated and hooked allowing for the whole system 200 to be pulled back against the hooked distal end of the articulating distal sheath 232. This may apply tension between the proximal filter 222 in the brachiocephalic artery 134 and the hooked end of the articulating distal sheath 232, pulling the intermediate section of the articulating distal sheath 232 up against the roof of the aortic arch 135 and the left common carotid artery 112.

FIG. 2G shows another method using a filter frame anchor 234. In this configuration, the distal filter 206 may include a filter frame anchor 234 to provide more surface area to contact the wall of the left subclavian artery 114. This may provide a similar mechanism to the design described in FIG. 2F, allowing for the system 200 to be pulled back against the filter frame anchor 234 and pulling the intermediate section of the articulating distal sheath 232 or other sheath up against the roof of the aortic arch 135.

As described above, the articulating sheath 232 can be actuated by pulling on a pull wire 251 that is attached to the distal end of the articulating distal sheath 232. This pull wire 251 is impeded off the central axis causing the sheath to deflect as the wire foreshortens. A similar mechanism may be employed in the deflector itself 220, as shown in FIG. 2H. By attaching pullwire(s) 251 off-axis to the deflector 220, the deflector's curvature and tilt may be controlled. Further details and embodiments of such a deflector 220 with a pull wire 251 are illustrated in FIGS. 2I-2K.

Figure 2I:
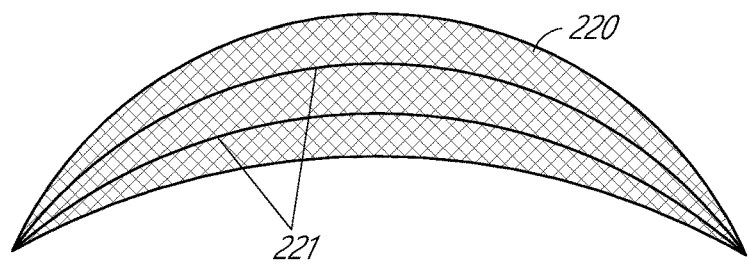
FIGS. 2I-2K schematically show the deployment of a deflector using the example shown in FIG. 2H.
Figure 2J:
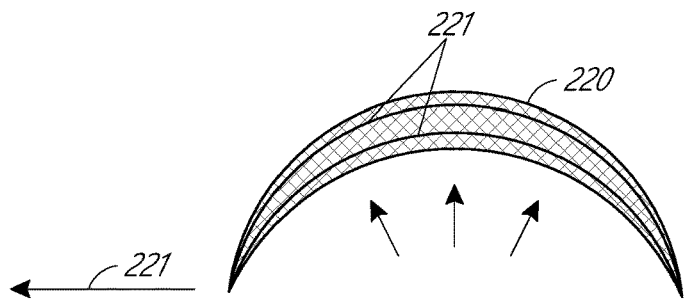
Figure 2K:
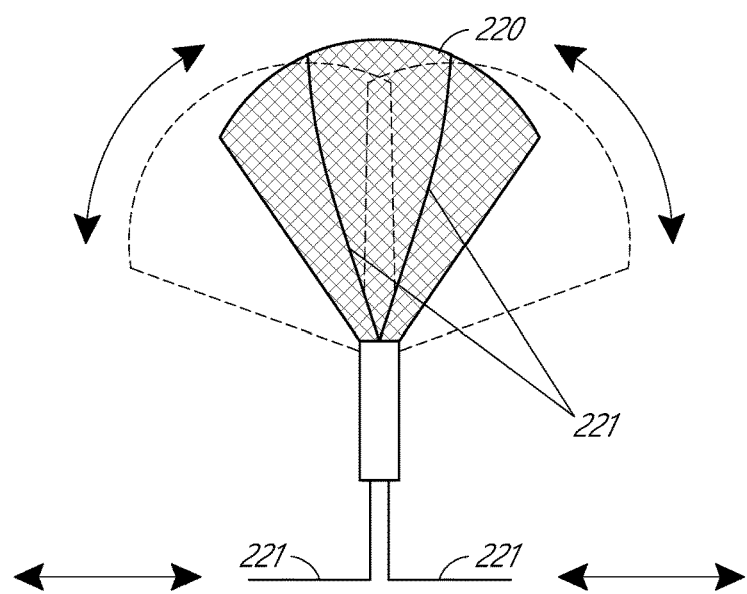

As shown in FIG. 2I, one or more pull wires 221 can extend through the deflector 220. The one or more pull wires 221 can be fixed to a distal end of the deflector 220. In FIG. 2J, as the pull wire(s) 221 are pulled proximally, the curvature of the deflector 220 increases. FIG. 2K shows an end view of the deflector 220. Selectively pulling the pull wires 221 will tilt the deflector 220 off-axis as shown by the dashed lines.

Figure 2L:
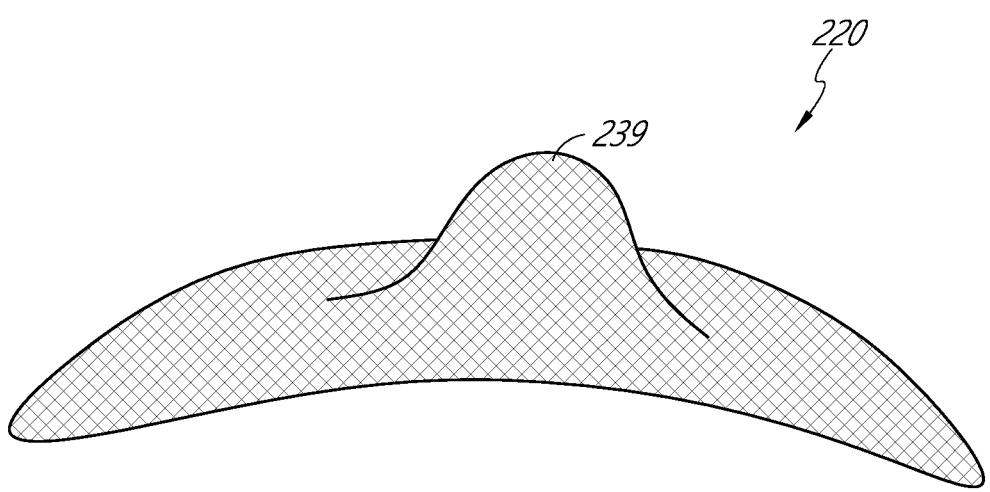
FIG. 2L shows an example of a deflector with a dome-shaped portion.

FIG. 2L illustrates a deflector design that can be used with any of the example systems described herein. The deflector 220 self-locates based on the shape of the deflector 220. For example, the deflector 220 can include a flexible dome shaped portion 239, such as in a central region of the deflector 220 where the diameter decreases toward the apex of the dome shaped portion 239. An apex of the dome shaped portion 239 can have a diameter of less than or equal to half of a diameter of a base of the dome shaped portion 239. For example, a base of the dome shaped portion 239 can have about a 12 mm diameter and an apex of the dome shaped portion 239 can have about a 5 mm diameter. The deflector 220 may seal against the vessel opening rather than the area around the vessel. In addition, this may provide position location feedback when attempting to place the deflector in the correct location.

Figure 2M:
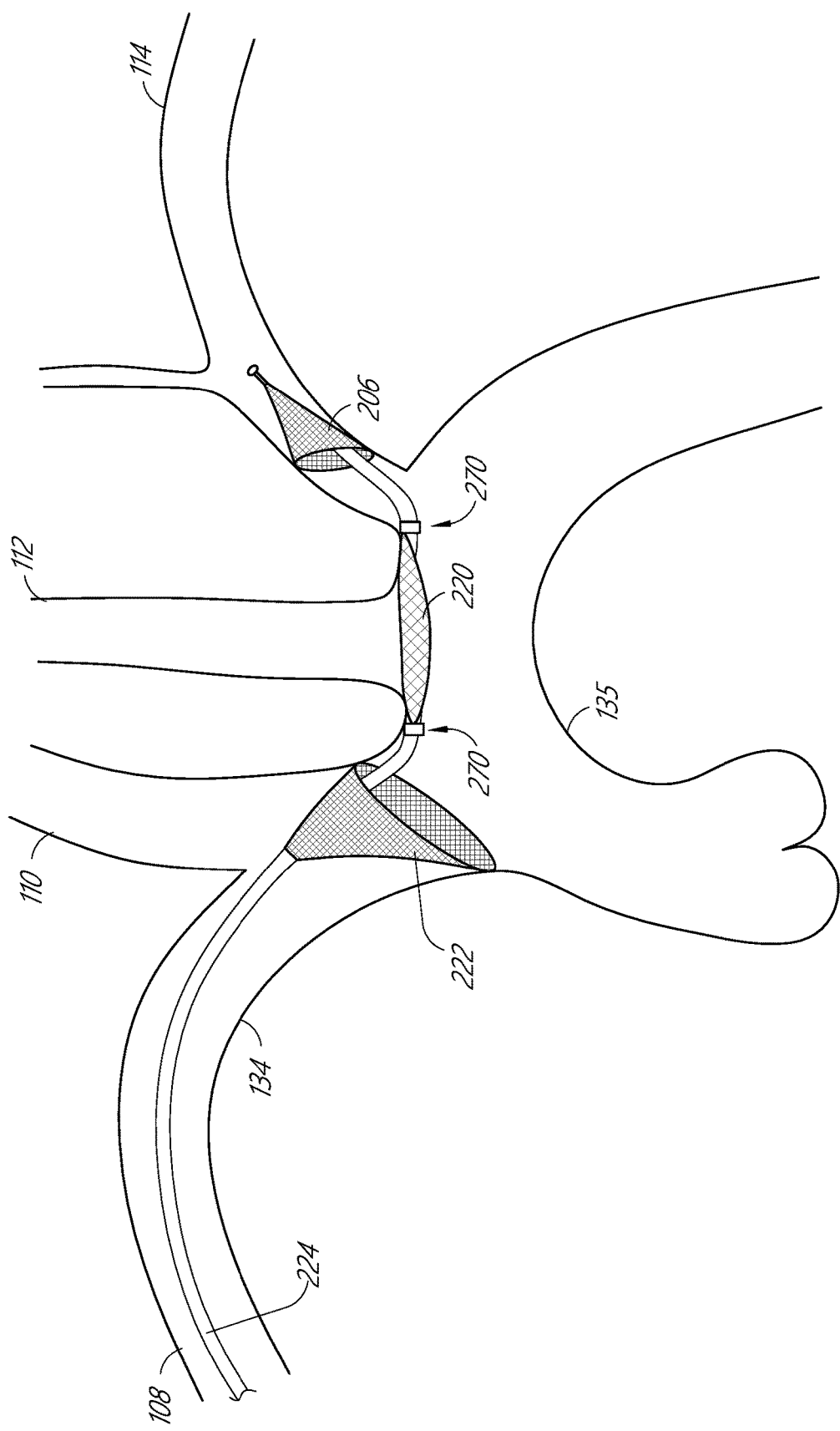
FIGS. 2M-2O show another example of a protection system that uses a deflector to block the left common carotid artery.
Figure 2N:
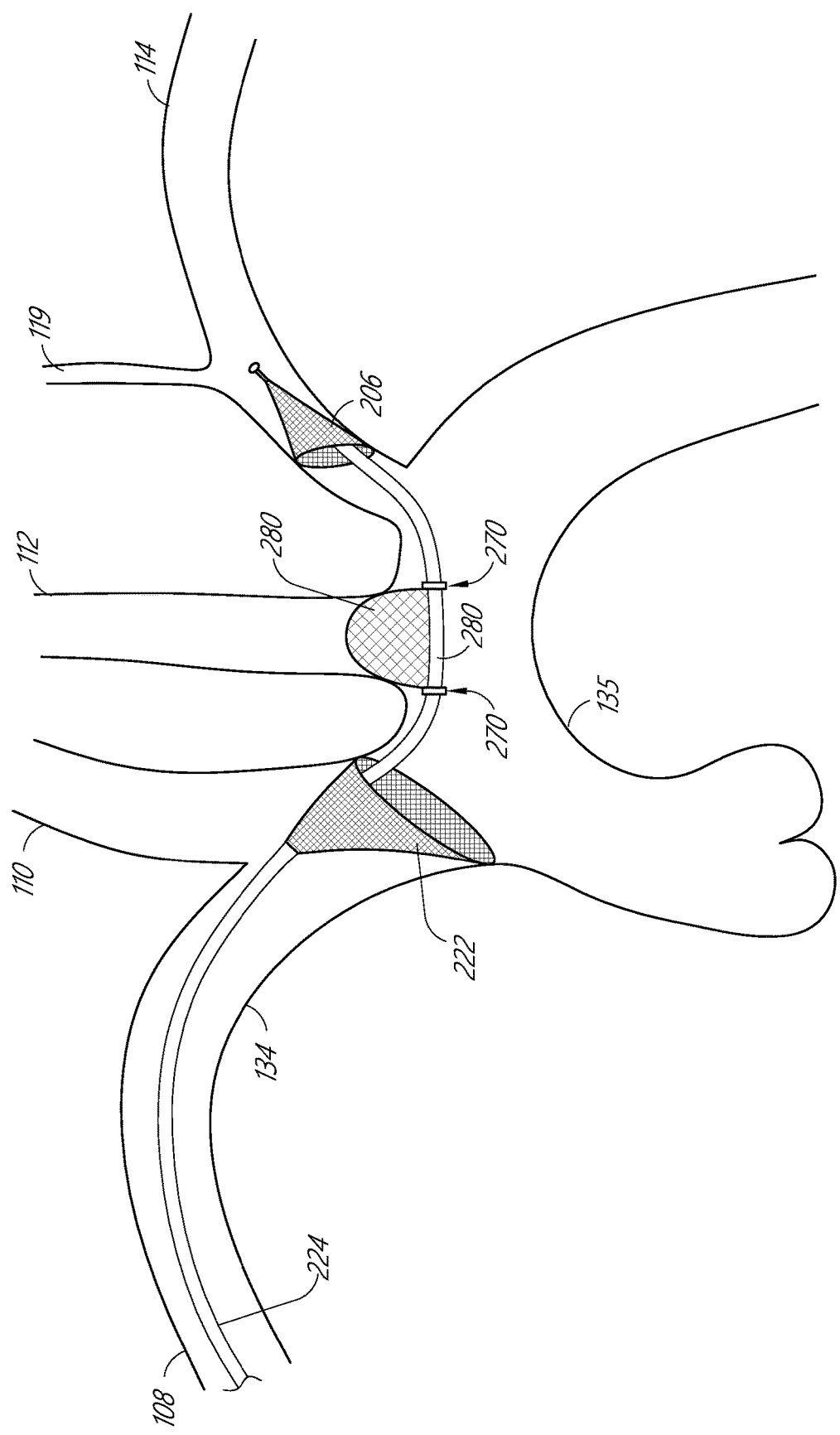
Figure 2O:
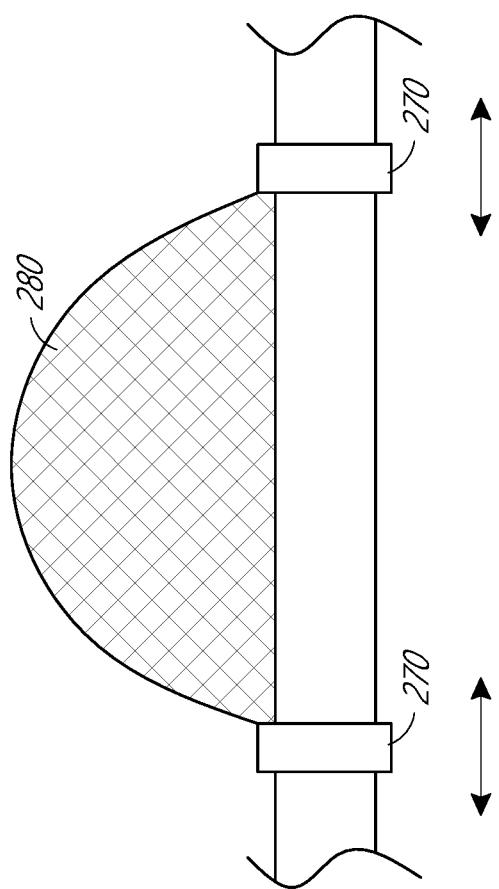

FIGS. 2M-2O illustrate another example protection system 200 with a deflector 220 that engages a greater surface area of a roof of the aortic arch 135. In this example, as shown in FIG. 2M, the deflector 220 can have one or both ends mounted to a slideable collar 270. The deflector 220 can be configured such that blood pressure can push the deflector 220 into the left common carotid 112 as shown in FIG. 2N. Additionally or alternatively, the slideable collar(s) 270 can be coupled to one or more pull wires (not shown) to foreshorten the deflector 220 and push the deflector 220 into the left common carotid 112 as shown in FIG. 2O.

Figure 3B:
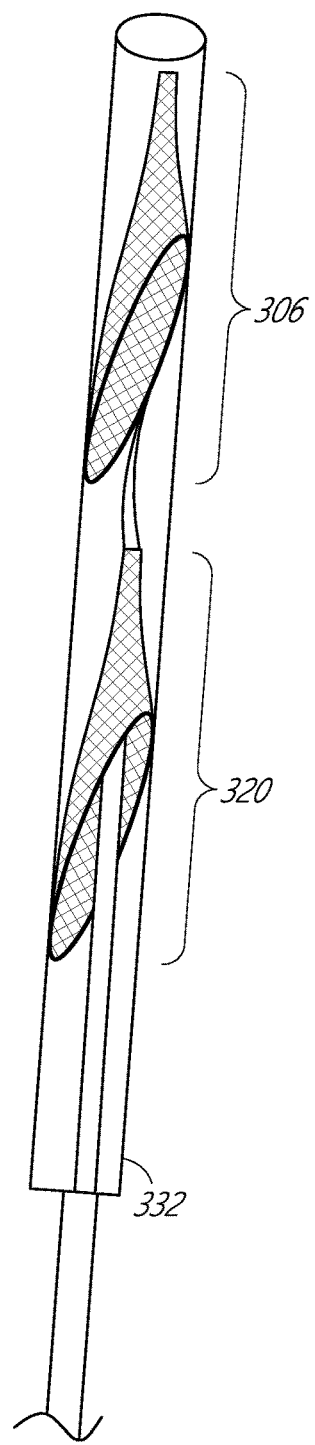

With reference to FIGS. 3A-3B, another illustrative embodiment of a protection system 300 is shown. The protection system 300 resembles the protection system 200 discussed above in many respects. Accordingly, numerals used to identify features of the protection system 200 are incremented by a factor of one hundred (100) to identify like features of the protection system 300. This numbering convention generally applies to the remainder of the figures. Any component or step disclosed in any embodiment in this specification can be used in other embodiments.

FIGS. 3A-3B illustrates yet another example protection system 300 in which two filters 306, 320 are serially loaded into the articulating distal sheath 332 that can be delivered to the aorta 135 via an outer sheath 324. As shown in FIG. 3B, the distal filter 306 and the secondary distal filter 320 can be loaded in the articulating distal sheath 332.

As shown in FIG. 3A, the proximal filter 322 can be placed in the brachiocephalic trunk 134. The articulating distal sheath 332 can be rotated, advanced/retracted, and/or articulated in order to allow for cannulation of a second and/or third vessel. The protection system 300 can utilize certain features such as the articulating sheath described in U.S. Pat. No. 9,492,264, which is hereby incorporated by reference herein, to place the secondary distal filter 320 in the left common carotid artery 112 and/or the distal filter 306 in the left subclavian artery 114. A first vessel can be cannulated, preferably the left subclavian artery 114, and the distal filter 306 can be deployed in the first vessel. This distal filter 306 can be detached from the articulating distal sheath 332 for later retrieval. Following placement of the distal filter 306, the tip of the articulating distal sheath 332 can be withdrawn, and the second vessel, preferably the left common carotid artery 112, can be cannulated, and a secondary distal filter 320 can be deployed in the second vessel. In order to remove the system, the secondary distal filter 320 can be first resheathed, and then a feature 307 on the detachable distal filter 306 can be recaptured by the articulating distal sheath 332. The proximal filter 322 that was placed in the brachiocephalic trunk 134 can be resheathed and the protection system 300 can be removed from the body.

In other configurations, the detachable distal filter 306 can be placed in the left common carotid artery 112, and the second filter 320 can be placed in the left subclavian artery 114. Instead of the right radial or brachial artery, the protection system 300 can also be inserted into the body through the left radial or brachial artery.

Figure 4A:
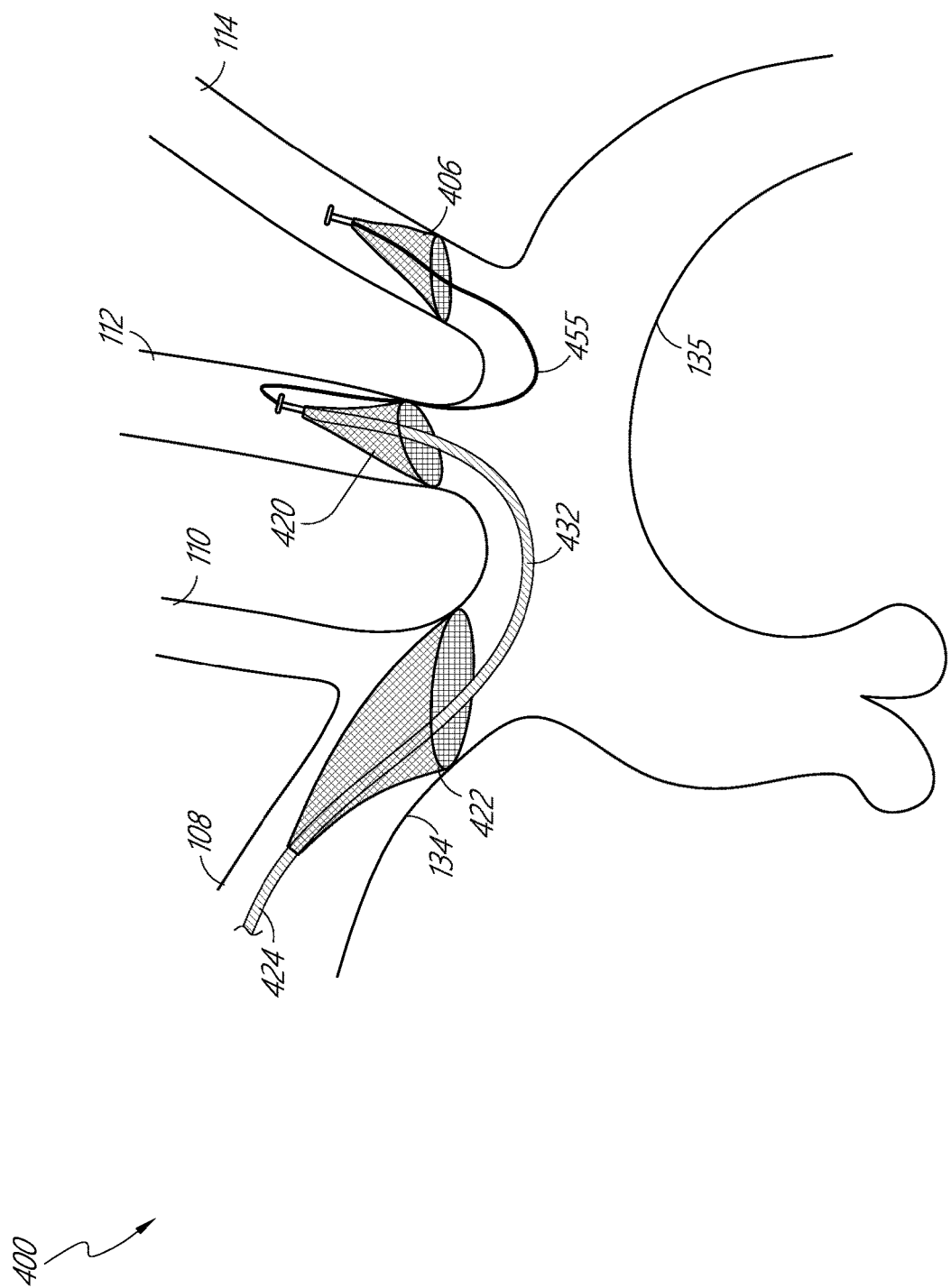
FIGS. 4A-4B show yet another example of a protection system in which the left subclavian and left common carotid filters are serially loaded into the articulating distal sheath and the aforementioned filters are tethered together.
Figure 4B:
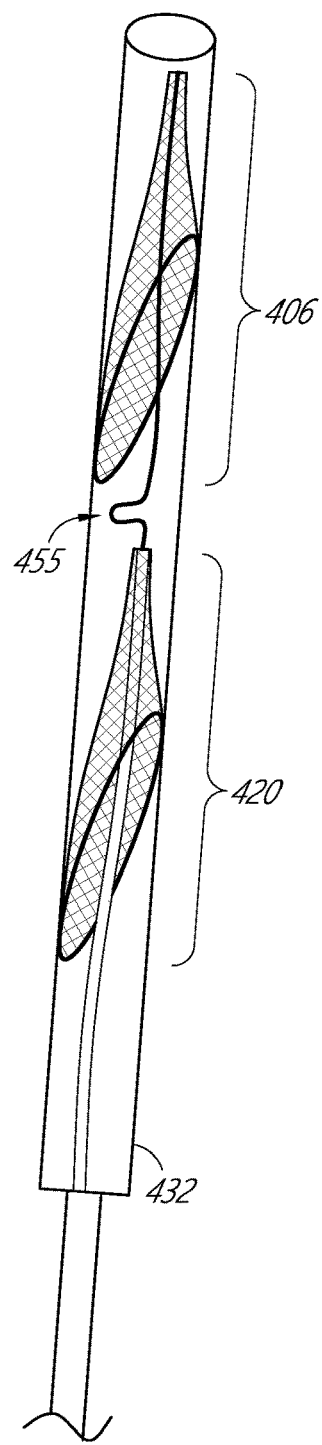

FIGS. 4A-4B illustrate another example protection system 400. Prior to deployment, the distal filter 406 and the secondary distal filter 420 can be loaded in the articulating distal sheath 432, as shown in FIG. 4B. A proximal filter 422 can be deployed in the brachiocephalic trunk 134. The left subclavian artery 114 can be cannulated with an independently steerable and positionable (e.g., rotatable and/or translatable) articulating distal sheath 432. A guidewire (not shown) can be utilized to facilitate positioning and to interrogate (e.g., visualize and assist in positioning) the vessel during cannulation.

A distal filter 406 can be deployed (e.g., by advancing the distal filter 406 or withdrawing the articulating distal sheath 432) in the left subclavian artery 114. The system 400 can utilize any of the features, such as the articulating sheath 432 described in U.S. Pat. No. 9,492,264, which is hereby incorporated by reference herein. Alternatively, the distal filter 406 can be placed in the left common carotid artery 112. The distal filter 406 can be connected to the articulating distal sheath 432 and/or the secondary distal filter 420 (still inside the tip of the articulating distal sheath 432) with a flexible tether 455. The flexible tether 455 can include a wire, an elastomeric material, nylon filament, suture, or other conformable attachment method.

Following placement of the first distal filter 406 in the left subclavian artery 114, the articulating distal sheath 432 can be withdrawn, and the second vessel, preferably the left common carotid artery 112, can be cannulated, so the secondary distal filter 420 can be deployed in the second vessel. The slack in the tether 455 may be pulled up against the vessel carina between the left common carotid artery 112 and the left subclavian 114 during deployment of the secondary distal filter 420 in the left common carotid artery 112.

In order to remove the system 400, the secondary distal filter 420 can be first resheathed, and then the distal filter 406 can be resheathed by withdrawing the tether 455 in order to pull the filter 406 into the tip of the articulating distal sheath 432. The proximal filter 422 that was placed in the brachiocephalic trunk 134 can be resheathed and the device 400 removed from the body. Alternatively, the distal filter 406 can be placed in the left common carotid artery 112, and then the secondary distal filter 420 can be placed in the left subclavian artery 114. Instead of the right radial or brachial artery, the protection system 400 can also be inserted into the body through the left radial or brachial artery.

Figure 5A:
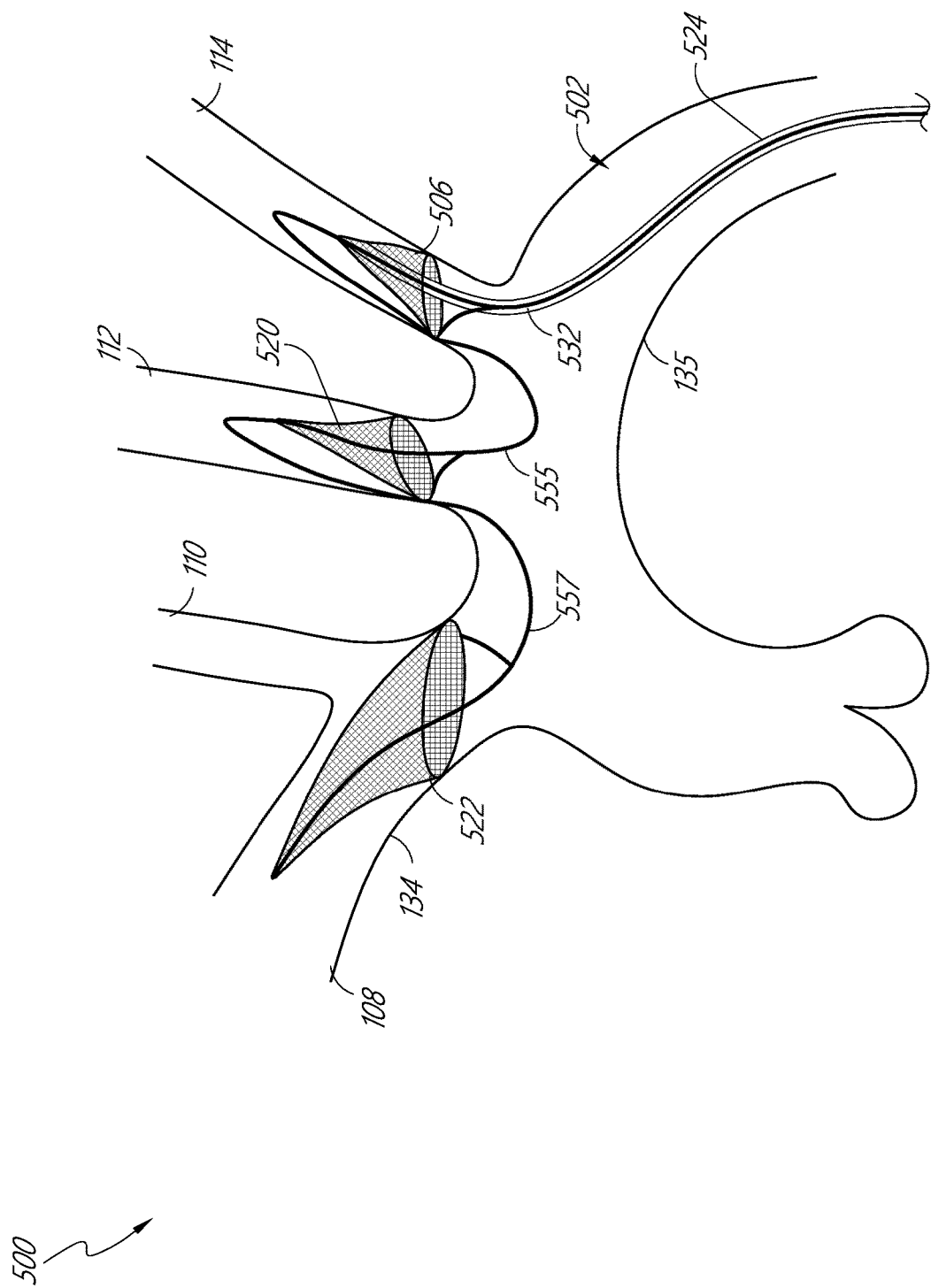
FIGS. 5A-5B shows another example protection system in which the system is introduced from the femoral artery and uses a three-tethered filter device.
Figure 5B:
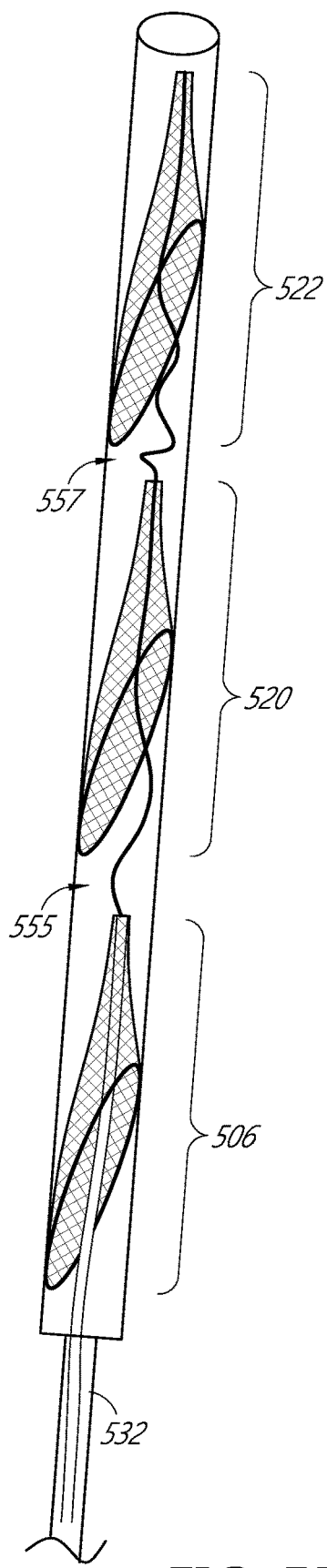

FIGS. 5A-5B illustrate another example protection system 500 in which three sequential filters 522, 520, 506 can be collapsed and loaded into a common delivery sheath 532. Because the example protection system 500 is delivered through the femoral artery, the system 500 can be sized up to at least 8 Fr or greater and only uses only two access sites for the TAVR procedure. In some implementations, a pigtail catheter for the index procedure can be integrated or incorporated into the example protection system 500, such that the pigtail catheter and the filters 522, 520, 506 are delivered from the same access site. The pigtail catheter can be delivered through the same sheath or introducer as the filters 522, 520, 506. Further, the example protection system 500 does not require retroflex cannulation. Although FIG. 5A illustrates the system 500 being delivered through the femoral artery, the system 500 can also be delivered via the right arm (e.g. right radial artery) or the left arm (e.g. left radial artery). The sizing and orientation of the filters would match the vessel diameters. For instance, in a femoral artery configuration, the apex of each filter shall be distal relative to the operator.

The proximal filter 522 may be delivered to the brachiocephalic artery 134, followed in order with the secondary distal filter 520 being delivered to the left common carotid artery 112, and the distal filter 506 being delivered to the left subclavian artery 114. A diameter of each filter opening would be approximately 8-17 mm for the brachiocephalic artery 134, 5-11 mm for the left common carotid artery 112, and 7-14 mm for the right subclavian artery 108. The filters 522, 520, 506 can be joined together by one or more tethering elements 555, 557. The tethering elements 555, 557 may form a continuous tether. The tethering elements 555, 557 can extend through a coaxial shaft 532. Alternatively, each filter 522, 520, 506 can include a filter frame supporting a filter membrane, and the tethering elements 555, 557 may be integrated into the filter frame and run within the filter membrane of one or more filters 522, 520, 506. The tethering elements 555, 557 may be elastomeric or elastomeric with a core that becomes axially rigid at a specified elongation. Alternatively, the tethering elements 555, 557 may comprise a wire, nylon filament, suture material, or other conformable material. The relative length and/or elasticity shall ensure that the tethering elements 555, 557 have sufficient tension to draw the tethering elements 555, 557 up against the vessel carina in order to minimize possible entanglement or interference with other procedural devices, e.g., diagnostic catheters, guidewires, TAVI delivery systems, etc.

Figure 6:
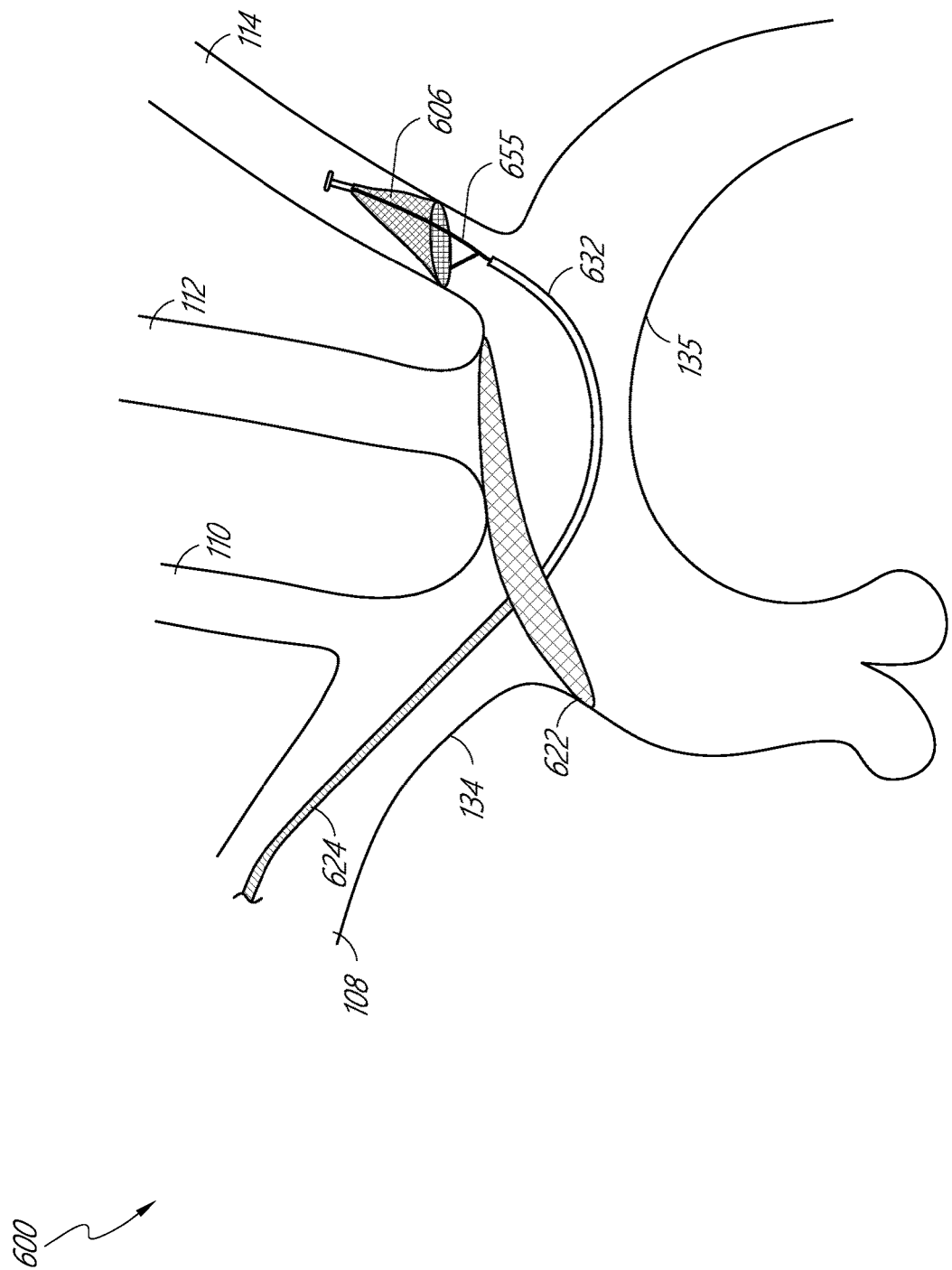
FIG. 6 shows another example protection system where the proximal filter is a deflector.
Figure 7A:
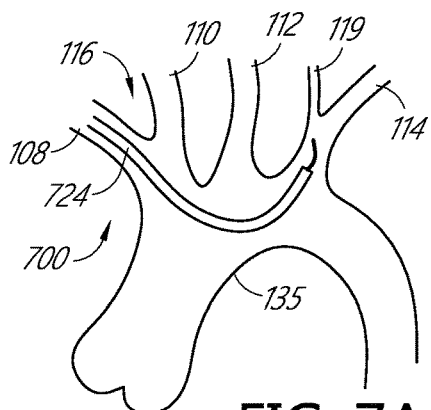
FIGS. 7A-7D show a method of deploying an example protection system having a single continuous strand design.
Figure 7B:
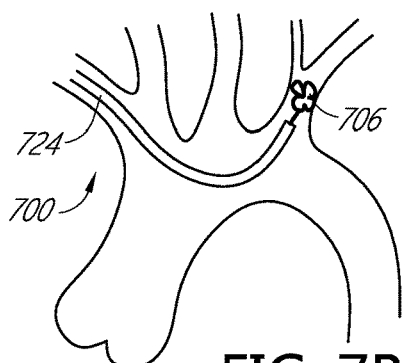
Figure 7C:
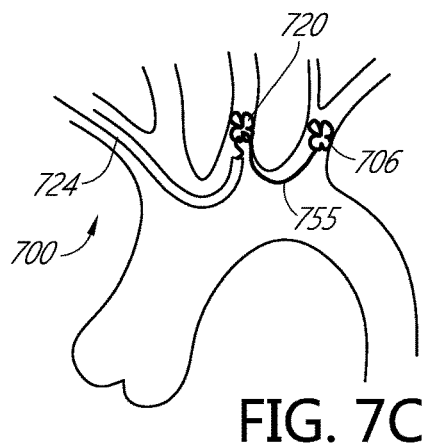
Figure 7D:
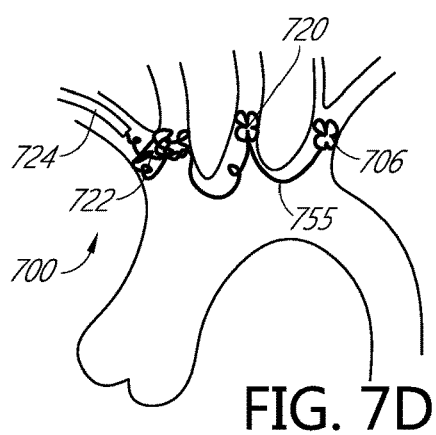
Figure 7E:
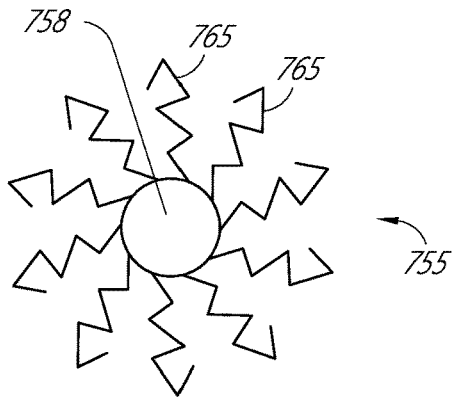
FIGS. 7E-7G show different cross-sections of the single continuous strand shown in FIGS. 7A-7D.
Figure 7F:
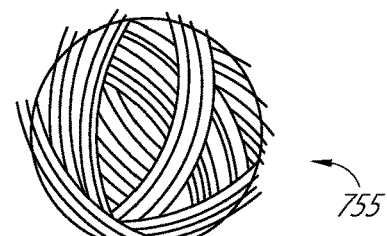
Figure 7G:
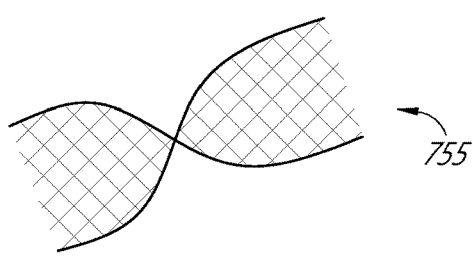

FIG. 6 illustrates another example protection system 600 having an aortic deflector 622. The deflector 622 can be mounted to the catheter shaft 624 using a pull wire, tether, or other structure. The deflector 622 can have a through-hole through which an articulating distal sheath 632 can be advanced. Deploying the distal filter 606 through the deflector 622 can be more advantageous than deploying the deflector 622 through a filter because the larger diameter catheter shaft 624 provides more support for the deflector 622 than the smaller diameter articulating distal sheath 632. Once the deflector 622 is deployed, tension applied to the catheter shaft 624 helps to seat the protection system 600 in the aorta 135, covering the ostium of the brachiocephalic trunk 134 and the left common carotid artery 112. The deflector 622 may be asymmetric with one lobe longer than the other relative with respect to the deflector through-hole. For example, the deflector 622 can include a first lobe configured to seal against an ostium of the left common carotid artery 112 and a second lobe configured to seal against an ostium of the brachiocephalic artery 134. A length of the first lobe can be measured from the deflector through-hole to an end of the deflector 622, and a length of the second lobe can be measured from the deflector through-hole to an opposite end of the deflector 622. The sealing perimeter of the deflector 622 may have a radiopaque feature such as a Platinum-Iridium coil. There may be a frame member embedded in the filter membrane of the deflector 622, or attached to the sealing perimeter of the deflector 622 to allow for adjustment to the deflector position in order to ensure a good seal and apposition to the vessel wall. One or more pull wires can be used to deflect the frame member embedded in the filter membrane or attached to the sealing perimeter to properly position the deflector 622.

Following deployment of the deflector element 622, the left subclavian 114 can be cannulated and a filter 606 can be deployed in the left subclavian artery 114 before the branch to the left vertebral artery 119 in order to ensure that blood flowing to the left vertebral 119 is filtered. The filter 606 can be mounted on a filter wire 655. The filter wire 655 may have a guide lumen to facilitate delivery over a guidewire. The filter 606 can be deployed by advancing the filter wire 655 or withdrawing the articulating distal sheath 632. Once deployed, the filter 606 is distal to the deflector 622. To remove the protection system 600, the filter 606 can be first sheathed, and then the deflector 622 can be sheathed.

Alternatively, the filter 606 can be first deployed in the left subclavian artery 114, and then the deflector element 622 can be deployed in the aortic arch 135. Instead of the right radial or right brachial artery, the protection system 600 can also be inserted into the body through the left radial or brachial artery. In this configuration, the deflector 622 element covers the left subclavian artery 114 and the left common carotid artery 112, and the filter 606 can be deployed in the brachiocephalic artery 134.

FIG. 7 illustrates another example protection 700 in which the device can accommodate a single, continuous strand 755 that can be fed out of the distal tip of a catheter 724. The fibrous strand 755 may have a pre-shaped core 758 causing three-dimensional forms 706, 720, 722 as the strand 755 is deployed. The pre-shaped core 758 may be a pre-shaped nitinol wire or other material with sufficient elastic properties to fill the space and block the vessels. External to the core 758, there may be protruding elements 765 that intertwine to form a fibrous filter 706, 720, 722. Alternatively, the filter elements 706, 720, 722 may be a pre-formed fibrous elements (FIG. 7F) or twisted weaves (FIG. 7G). During or prior to retrieval, the retrieval catheter 724 or a separate aspiration catheter may be used to aspirate any captured debris. These filters 706, 720, 722 formed of a single continuous strand 755 may be placed in the order of the left subclavian artery 114, then left common carotid artery 112, and finally the brachiocephalic trunk 134. Alternatively, the order may be reversed. Alternatively, the device may be inserted in the left brachial or radial artery rather than the right.

FIGS. 8A-8D illustrate another filter design that can be used in any of the other embodiments described herein, but for purposes of illustration, are shown in connection with a system similar to protection system 500. Here, the filter elements 806, 820, 822 are elongated when collapsed and axially foreshortened when deployed (see partial enlarged view in FIG. 8B), such that the greatest cross-section area of each filter 806, 820, 822 is in the mid-section of the respective filter. This configuration may allow for minimizing the profile of each filter, possibly minimizing the number of catheter exchanges during delivery and retrieval. The filter may be formed of wire mesh, like a "Chinese finger puzzle," formed of nitinol wire, laser cut, formed of polymer coated wire, or otherwise. One or more of the filters 806, 820, 822 can be foreshortened by using a pre-shaped filter design. Additionally or alternatively, a pull wire can be attached to either end of the filter. Moving one end of the filter relative to the other end of the filter can cause the filter to foreshorten.

Figure 8A:
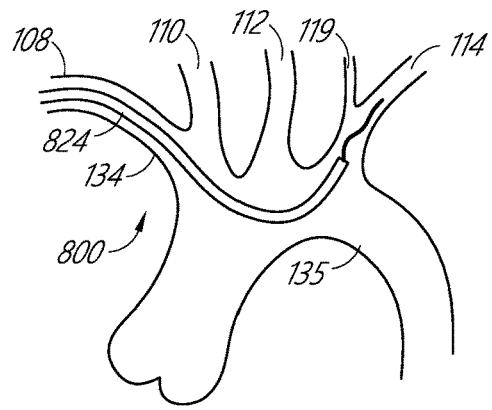
FIGS. 8A-8D show another example of a filter design that can be used with any protection system described herein.
Figure 8B:
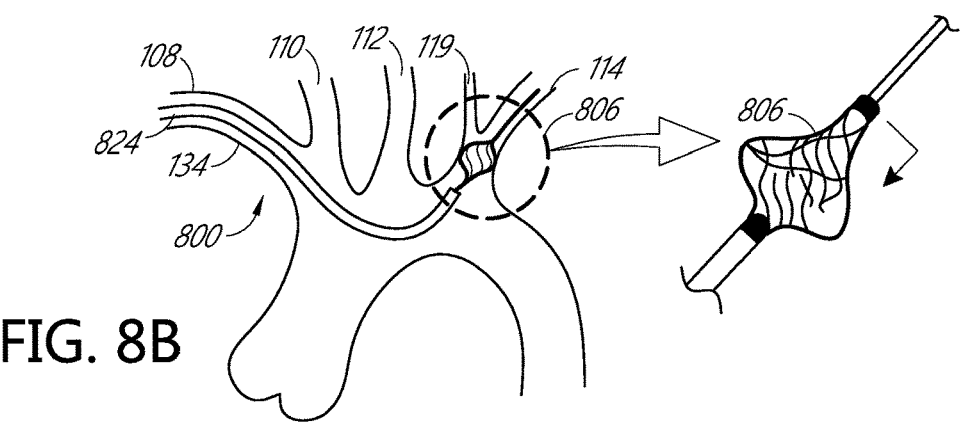
Figure 8C:
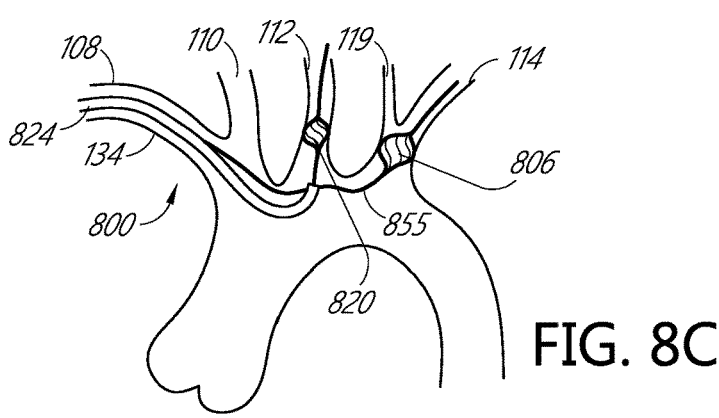
Figure 8D:
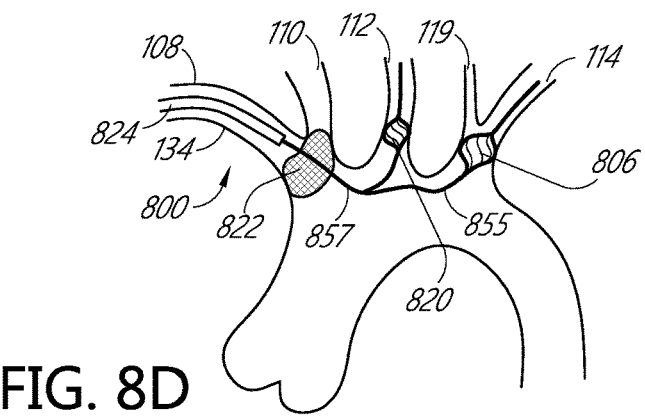

As shown in FIGS. 8A-8B, the left subclavian artery 114 can be cannulated, and then a distal filter 806 can be deployed in the left subclavian artery 114. As shown in the partial enlarged view in FIG. 8B, the distal 806 filter foreshortens upon deployment. Thereafter, the left common carotid artery 112 can be cannulated, and a secondary distal filter 820 can be deployed in the left common carotid artery 112, as shown in FIG. 8C. Finally, a proximal filter 822 can be deployed in the brachiocephalic artery 134, as shown in FIG. 8D. The proximal filter 822 may have a larger deployed diameter than the distal filter 806 and/or the secondary distal filter 822. Each of the filters 806, 820, 822 can be connected together by a flexible tether 855, 857. In other configurations, the system 800 may be deployed from the left radial or left brachial artery and the filters 806, 820, 822 can be deployed in reverse order.

FIGS. 8E-8L illustrate another variation of the design of the filters used in any of the previous embodiments described herein. This filter design creates additional space in the catheter to accommodate controls for the deflector. The filter 888 can be foreshortened using any of the techniques described above with respect to FIGS. 8A-8D. The filter 888 can include a ring 883 that holds the filter 888 in a proper position in the vessel wall. As tension is applied to the system or the pull rod 886 is pulled back, a proximal side of the filter 888 becomes concave while the ring 883 maintains the filter 888 in the same position.

FIGS. 8G-8L illustrate a method of deploying the filter 888. In the sheathed configuration, the filter 888 can be positioned within the sheath 889 (see FIGS. 8G and 8L). To unsheath the filter 888, the push rod 886 can be moved distally while the slotted tube 890 is kept stationary. As the push rod 886 is moved distally, the sheath 889 is moved distally to reveal the filter 888 (see FIG. 8K). The push rod 886 can include one or more flanges 892 that can push a proximal end of the filter to foreshorten the filter 888. There can be a ring 887 welded to secure the push rod 886 to the sheath 899. A benefit to this approach is that upon re-sheathing the filter 888, the sheath 899 pushes against the filter 888 from the distal side, this may collapse the filter 888 against the blood flow, ensuring that any particulate is held by the filter and moves inward toward the central lumen.

Figure 9A:
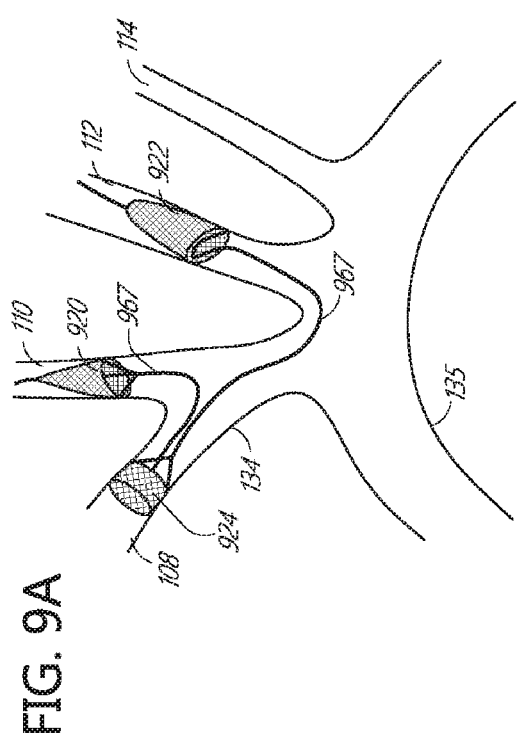
FIG. 9A shows another example protection system that uses detachable filters having a docking functionality.

FIG. 9A illustrates another example protection system 900 in which a guidewires 967 can be placed into each respective vessel. The guidewires 967 can have a distal feature that allows the filters 924, 922, 920 to become permanently affixed once the filters 924, 922, 920 and delivery catheter are advanced coaxially in an over-the-wire technique. The guidewires 967 may have a pre-shaped element, for example nitinol, to form the span between the vessels. As shown in the figures, this design allows a bare guidewire 967 to be placed in each target location with standard guidewire placement techniques either though a guide catheter, through bare wire manipulation, etc. Once the guidewire 967 is in place, a filter 920, 922, 924 can be introduced over its respective guidewire 967, slid into the target location, and activated to dock the filter 920, 922, 924 onto the guidewire 967. This process can be repeated for each filter 920, 922, 924. One of the filters 920, 922, 924 or an additional filter could be placed in the same way in the left subclavian artery 114.

FIG. 10A-10H shows an example of an aortic filter system 1000. Rather than locate the protection system at the aortic arch 135, the brain may be protected by filtering in the ascending aorta 137. This approach can protect all three vessels to the brain with one filter 1022 deployed from a catheter 1024. The catheter delivery system for the index procedure can be accommodated by the filter 1022 so as to retain good wall apposition as the system crosses the filter 1022.

To accommodate the procedural catheter 1045 in this filter design, several design attributes have been identified to enable the filter 1022 to still seal while having another index procedure catheter 1045 occupy the same space in the vasculature. The filter 1022 may not be continuous around the circumference of the filter and may instead be separated into overlapping petals 1041, 1044, like those of a flower bloom, so that the overall structure and shape of the filter 1022 is not disturbed by the presence of another catheter 1045. FIGS. 10A-10G illustrate certain features of such an aortic filter system 1000.

Figure 10A:
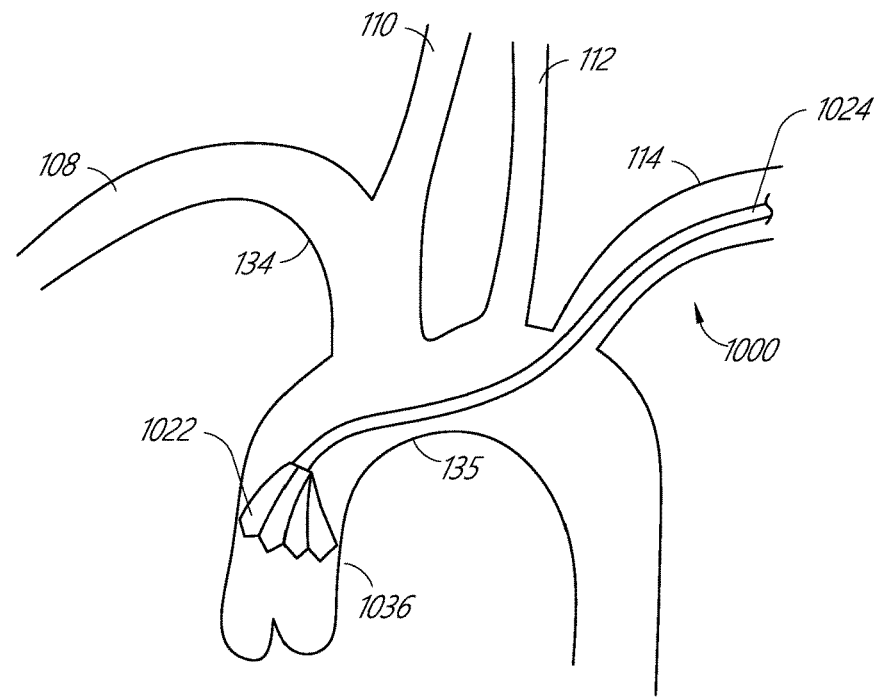
FIGS. 10A-10I show an example of an aortic filter system.
Figure 10B:
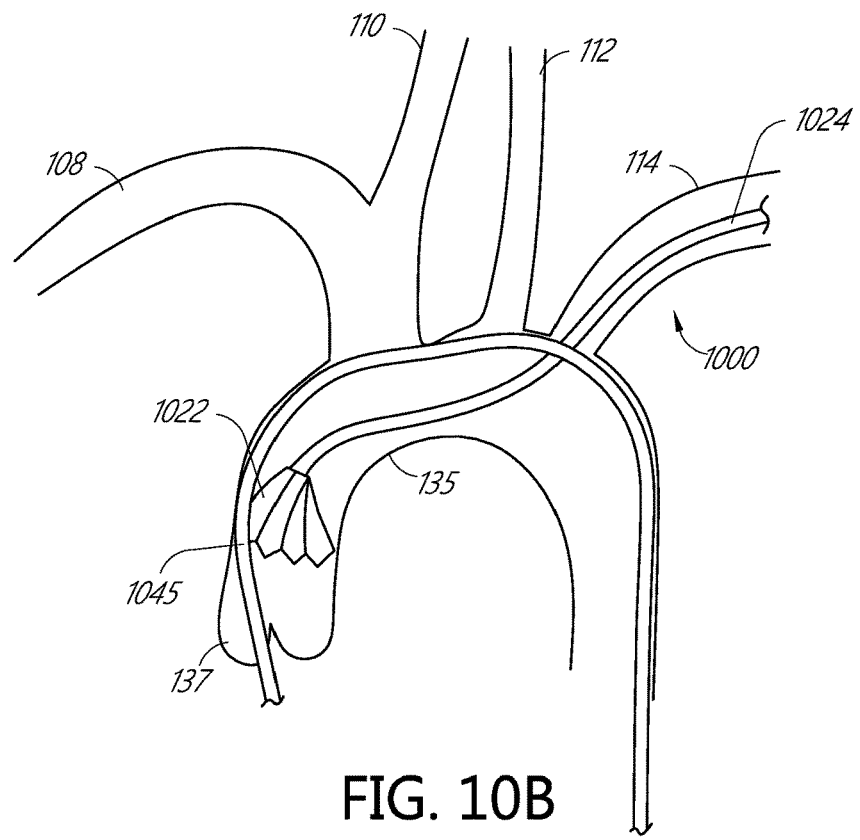

FIG. 10A illustrates the aortic filter system 1000 positioned in the ascending aorta 137. FIG. 10B illustrates the system 1000 positioned in the ascending aorta with another procedural catheter 1045 operating in the same space. As shown in FIGS. 10C-10G, this can be accomplished by having two concentric rings of filter petals configured to be deployed from the actuation shaft 1024—an inner ring 1053 and an outer ring 1054. The inner ring 1053 can be located more distal on the shaft 1040 than the outer ring 1054 such that a distal end of the outer ring 1054 extends beyond a distal end of the inner ring 1053. Alternatively, the inner and outer rings 1053, 1054 can be attached to the shaft 1040 at the same axial position, but the outer petals can have a different length than the inner petals.

Figure 10C:
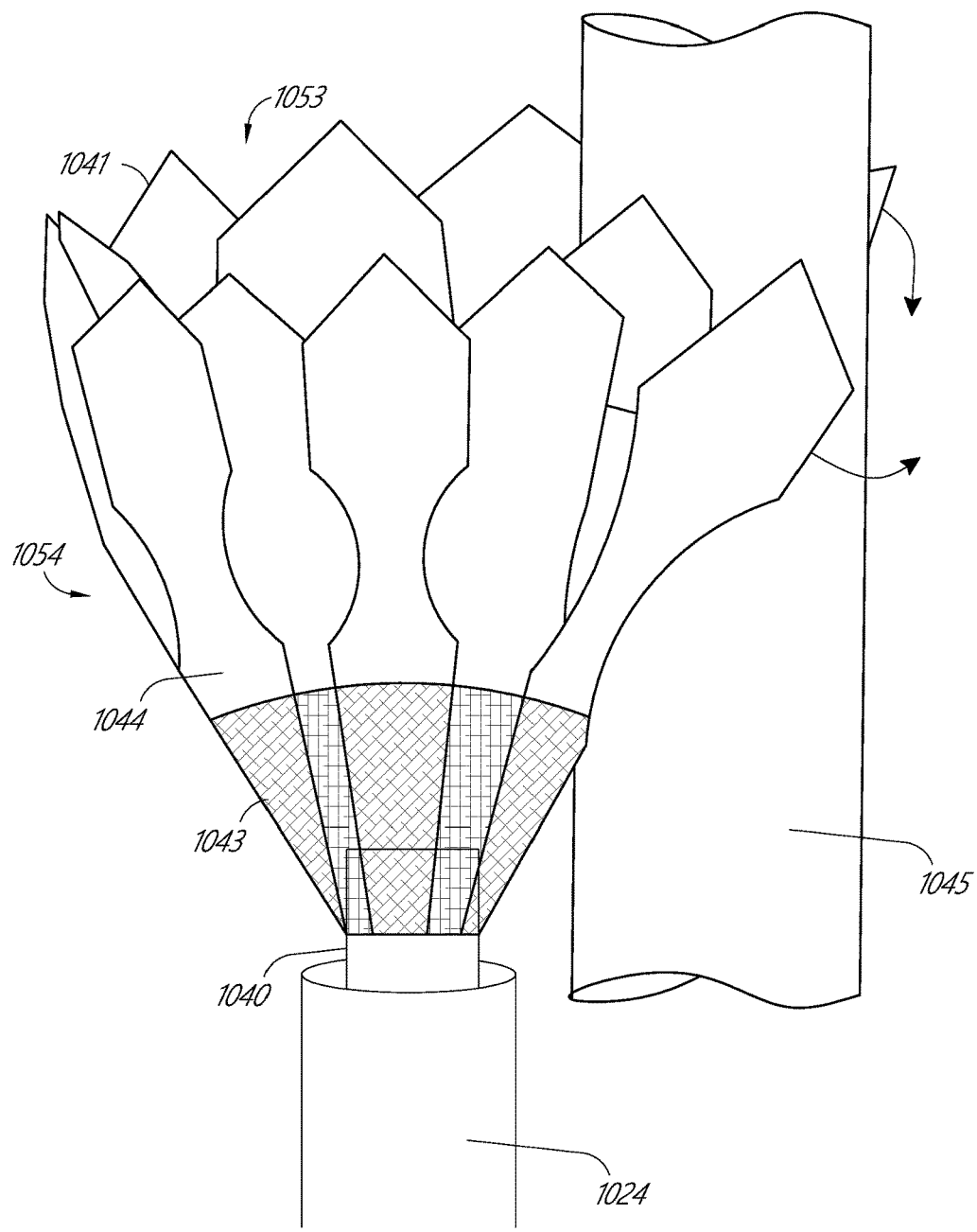
Figure 10D:
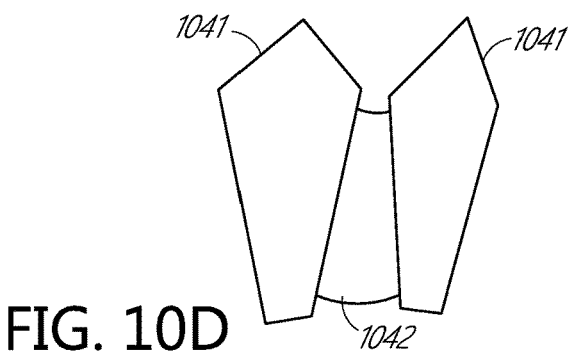
Figure 10E:
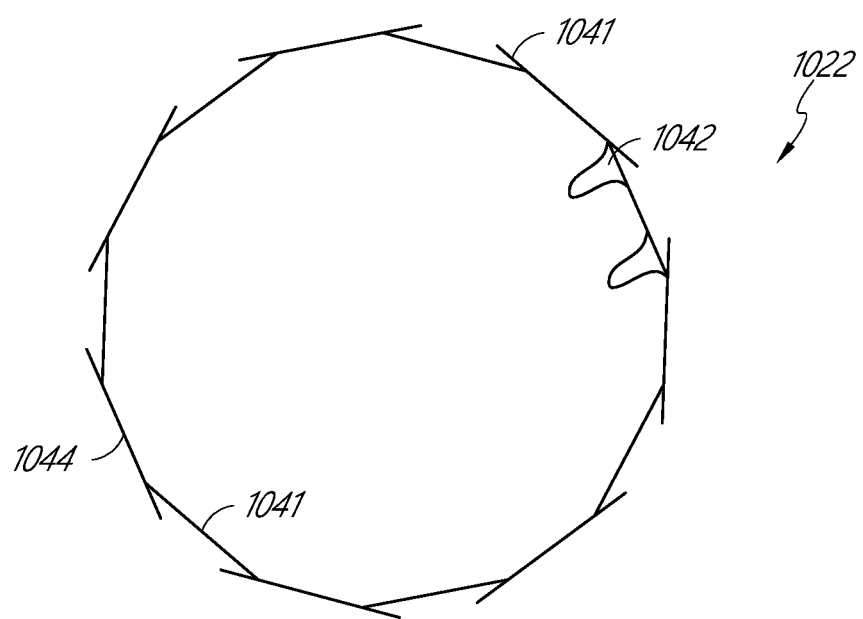

As shown in FIGS. 10C through 10E, the system 1000 can also include webbing 1042 that exists between the inner and outer petals in the region of the filter 1022 where the procedural catheter 1045 is expected to extend. The webbing 1042 can be loose, with extra material when the index procedure catheter 1045 is not present. The webbing 1042 can have a same material as the inner and/or outer petals. However, when the procedural catheter 1045 is present, this allows for the inner petal 1053 to move toward the lumen of the filter 1022, while still maintaining a continuous seal with the procedural catheter 1045, as shown in FIG. 10C. Radiopaque markers 1052 can be applied to petals help to identify where on the circumference of the filter 1022 the catheter 1045 can be accommodated (see FIG. 10F).

Figure 10F:
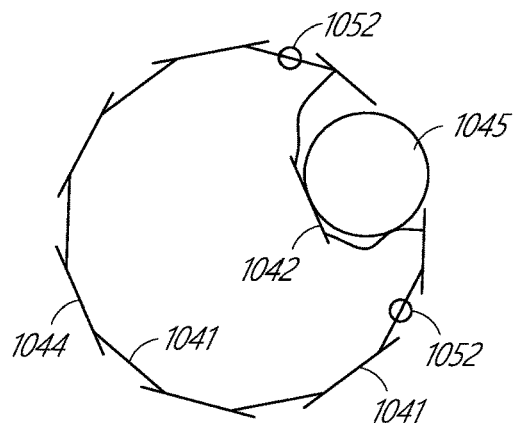
Figure 10G:
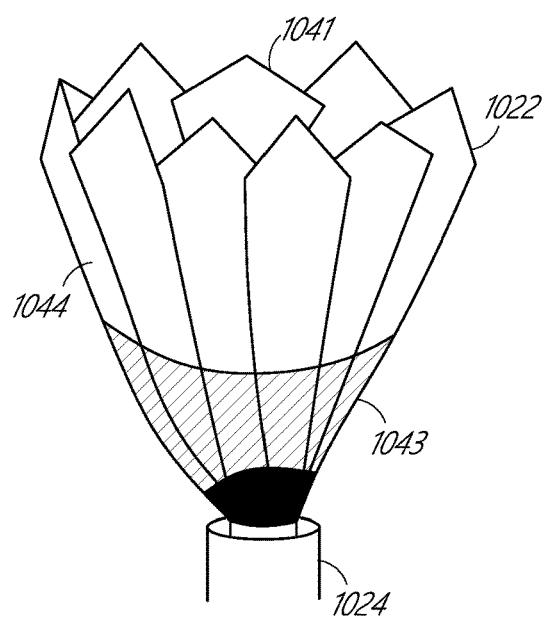

As shown in FIGS. 10C and 10G, the system 1000 can include a waistband 1043 that is connected to each of the outer petals 1044 near the base of the petals. This waistband 1043 serves to draw the outer petals 1044 together when the procedural catheter 1045 pushes the waistband 1043 inward toward the central lumen of the catheter 1024. This feature aids in wrapping the outside edge of the procedure catheter 1045 with the filter 1022 and tightens the webbing 1042 discussed earlier against the procedural catheter 1045. The waistband 1043 can be the same or different material as the inner and/or outer petals. For example, the waistband 1043 can be a wire mesh or polyurethane mesh.

Figure 10H:
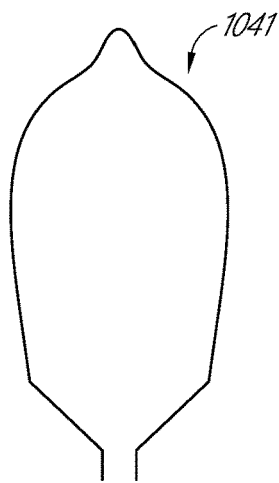
Figure 10I:
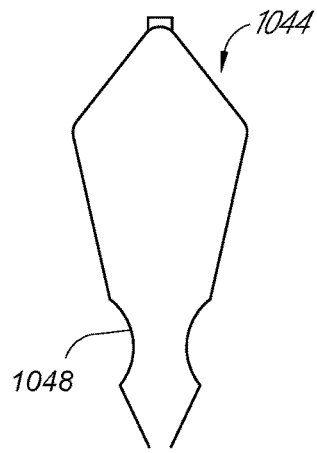

FIGS. 10H-10I illustrate the shape of the inner and outer petals. The outer petals 1044 (FIG. 10I) that are designed to rest against the procedural catheter 1045 are profiled to accommodate the cylindrical shape of the procedural catheter 1045, as shown in FIG. 10F. For example, each outer petal 1044 can include one or more scalloped or notched features 1048 on each lateral side of the petal 1044 to accommodate the procedural catheter 1045. Those petals in the inner ring 1041 (FIG. 10H) can be of a different shape and much wider in the circumferential direction than the outer petals 1044 to fill gaps as the outer petals 1044 shift to accommodate the catheter 1045. Therefore, the petals take a shape similar to those drawn in FIGS. 10C and 10G.

FIGS. 11A-11K shows an example protection system 1100 that can be inserted through the right radial or brachial artery. Although, the protection system 1100 can also be inserted through the left radial or brachial artery.

The protection system 1100 can include a dual filter assembly 1102 in which a first filter 1122 can be deployed in the brachiocephalic trunk 134 and a second filter 1120 can be placed in the left common carotid artery 112. The dual filter assembly 1102 can be arranged as disclosed in U.S. Pat. No. 9,492,264, which has been incorporated by reference herein and can be deployed utilizing the same or similar steps. The left subclavian artery 114 can be provided with a distal accessory filter 1106.

Figure 11A:
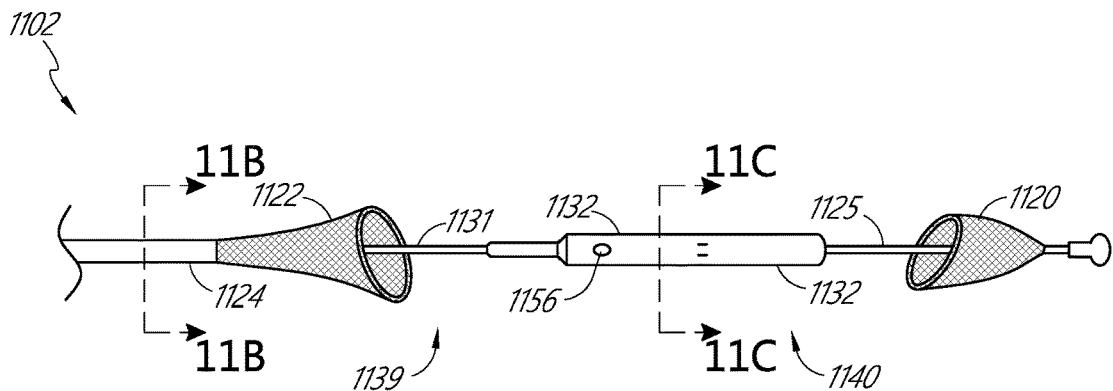
FIGS. 11A-11S illustrate another protection system with an alternative accessory filter that can be inserted through the right radial or brachial artery to the left subclavian artery.
Figure 11B:
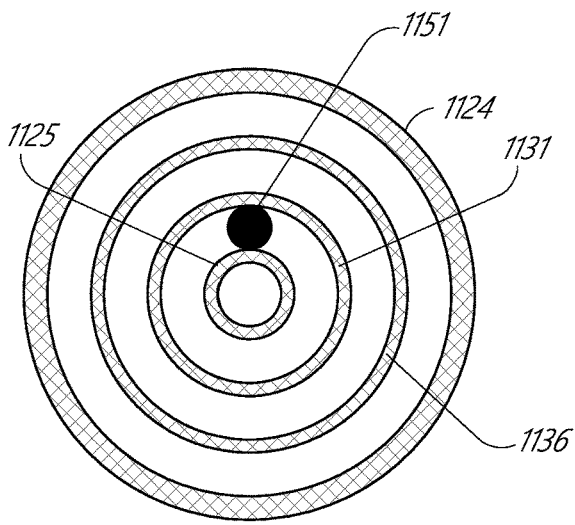
Figure 11C:
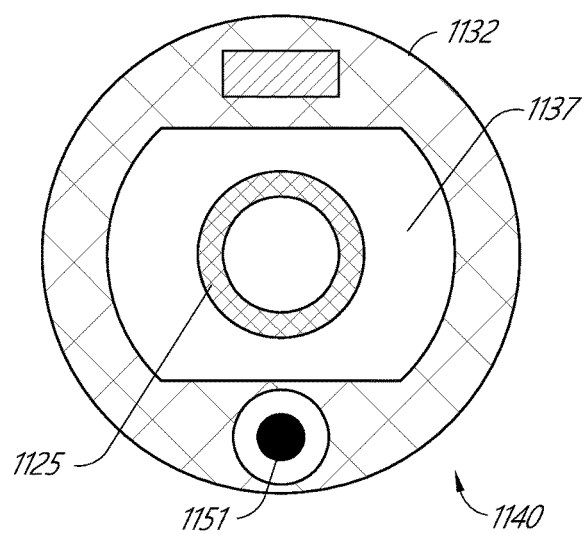

As shown in FIG. 11B, a cross-section through line 11B-11B shows a proximal terminating tube 1136 of proximal filter 1122 positioned radially inward of the outer sheath 1124, a shaft 1131 of the articulating distal sheath 1132 positioned radially inward of the proximal terminating wire or tube 1136, and the distal filter shaft 1125 positioned radially inward of the shaft 1131 of the articulating distal sheath 1132. The distal filter shaft 1125 carries the secondary distal filter 1120. A pull wire 1151 extends in a space between the distal filter shaft 1125 and the shaft 1131 of the articulating distal sheath 1132 or through a wall of the shaft 1131 of the articulating distal sheath 1132. As shown in FIG. 11C, a cross-section taken through line 11C-11C shows the articulating sheath 1132 with the pull wire 1151 extending through the wall of the articulating distal sheath 1132 and the distal filter shaft 1125 positioned radially inward of the articulating distal sheath 1132. The distal accessory filter 1106 is mounted on a filter wire 1125 that extends through the space 1137 between the articulating distal sheath 1132 and the distal filter shaft 1125.

Figure 11D:
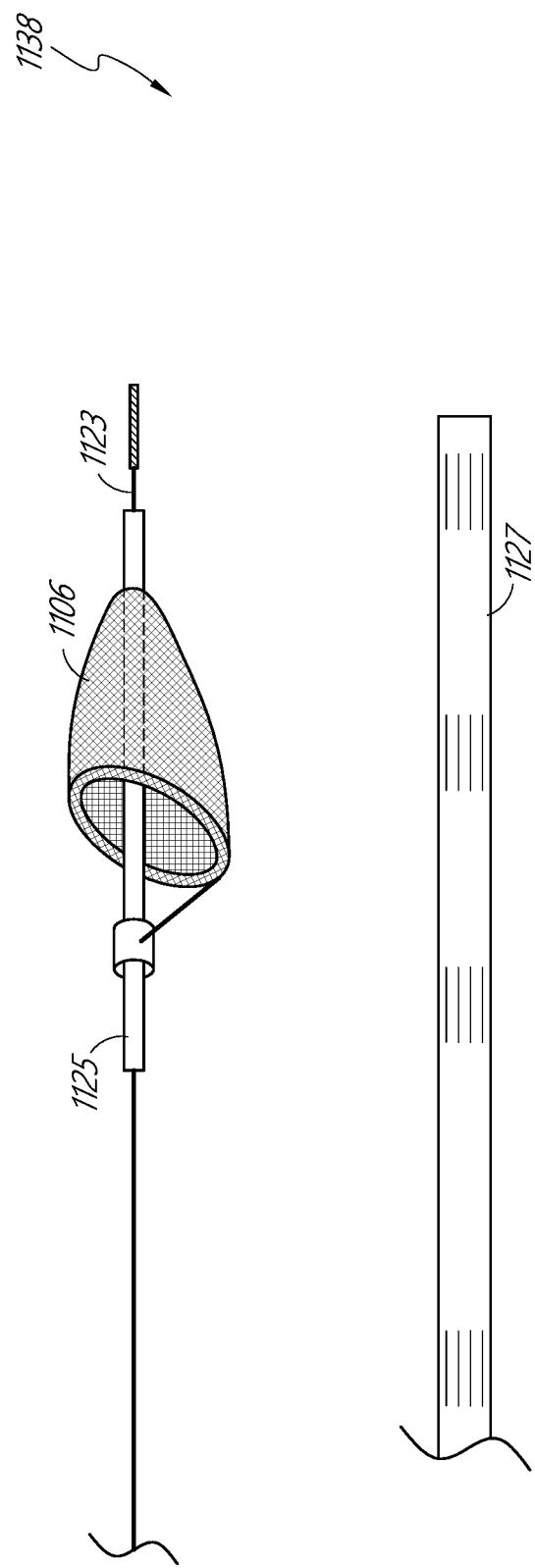

FIG. 11D shows a component of a distal filter accessory assembly 1138. The distal filter accessory assembly 1138 can include a distal filter 1106 mounted on a filter wire 1125. The filter wire 1125 can have a guide lumen for delivery over a guidewire 1123. The filter wire 1125 can be independently steerable. Additionally or alternatively, the distal filter 1106 can be delivered through a filter sheath 1127. The filter sheath 1127 may have a pre-set curve shape or be deflectable using any features of the above-described articulating distal sheaths.

Figure 11E:
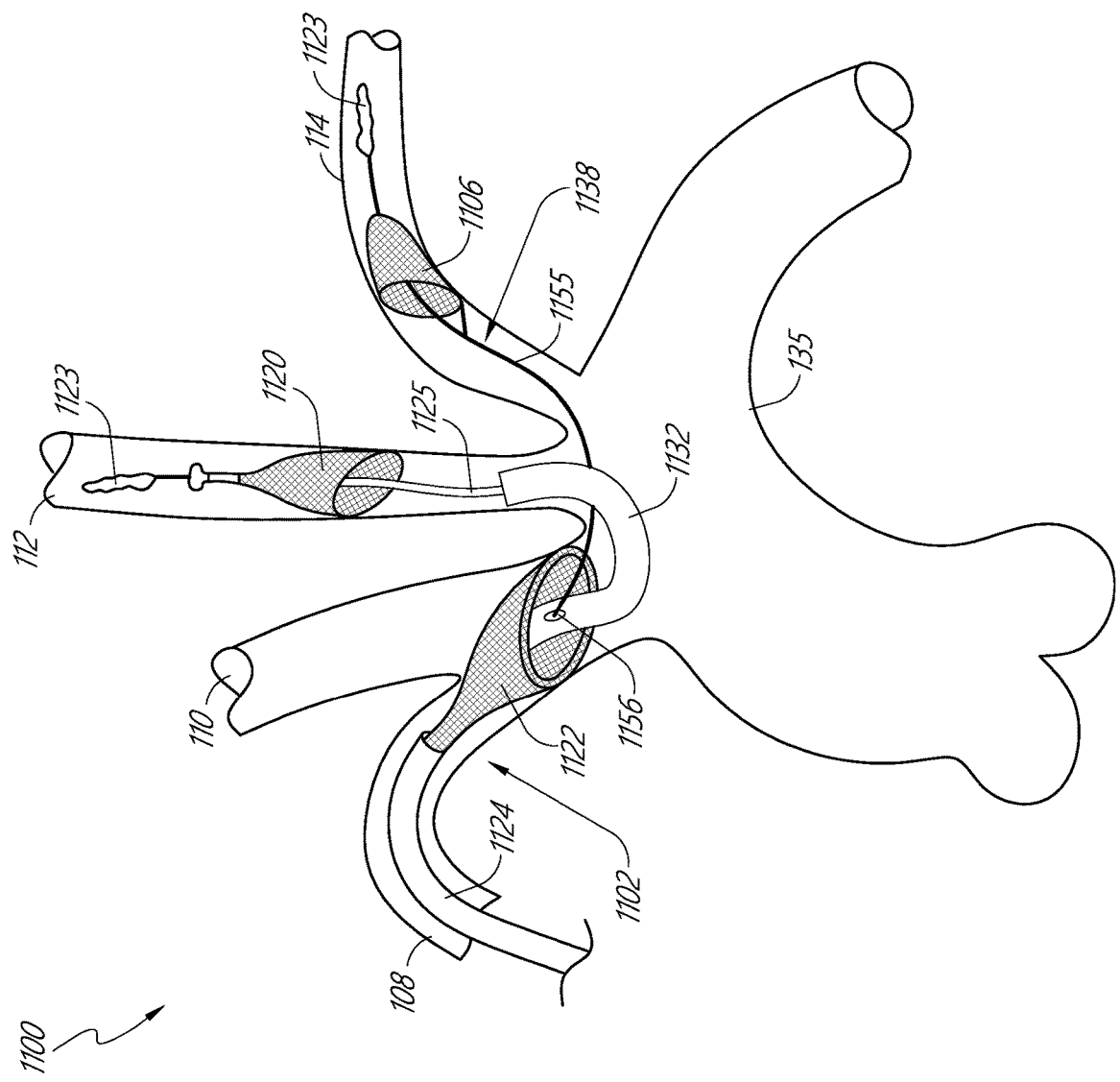
Figure 11F:
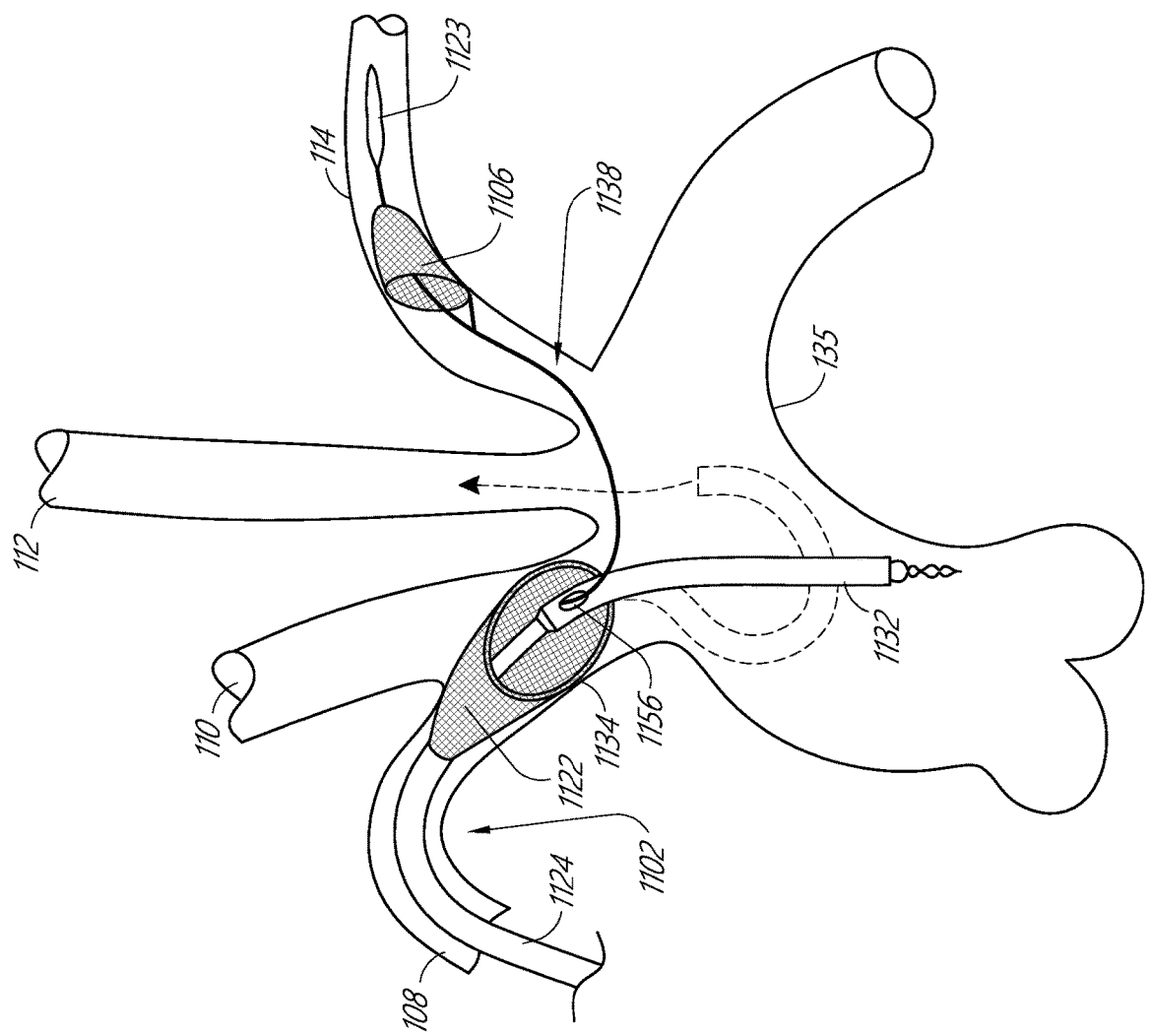

As shown in FIG. 11E, when fully deployed, the filter wire 1155 can extend through a port 1156 in the articulating distal sheath 1132. FIG. 11F shows the distal filter 1106 and the proximal filter 1122 being deployed before the articulating distal sheath 1132 cannulates the left common carotid artery 112, but in other configurations, the secondary distal filter 1120 may be deployed before the proximal filter 1122 and/or the distal filter 1106.

As shown, in FIG. 11F, in this example, the distal accessory filter 1106 can be delivered into the left subclavian artery 114. The articulating sheath 1132 can be delivered over the distal filter accessory assembly 1138 with the distal filter accessory assembly 1138 extending out of a port 1156 in the articulating distal sheath 1132. The filter sheath 1127 can be delivered through a guide catheter 1128 or include articulating features for steering, such as those described with respect to the above-described articulating distal sheaths. Alternatively, the filter sheath 1127 may have a pre-set curve shape or be deflectable.

Figure 11K:
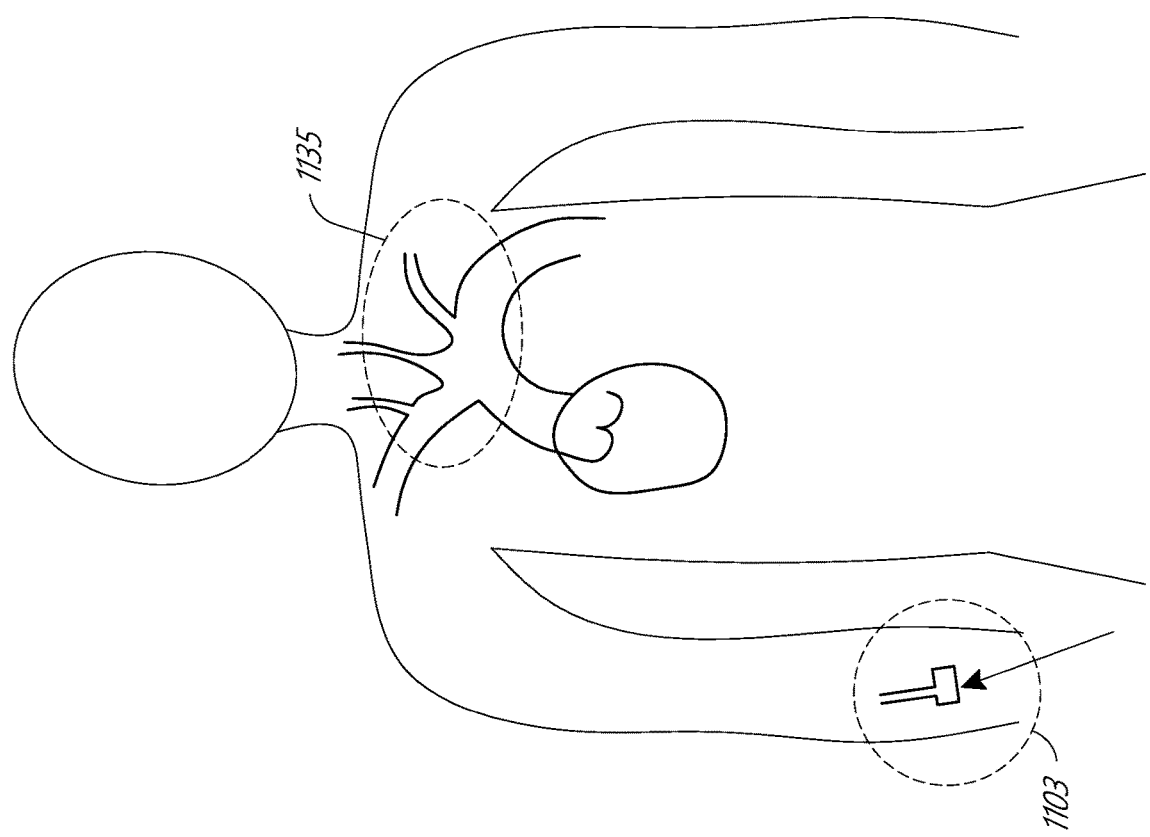
Figure 11M:
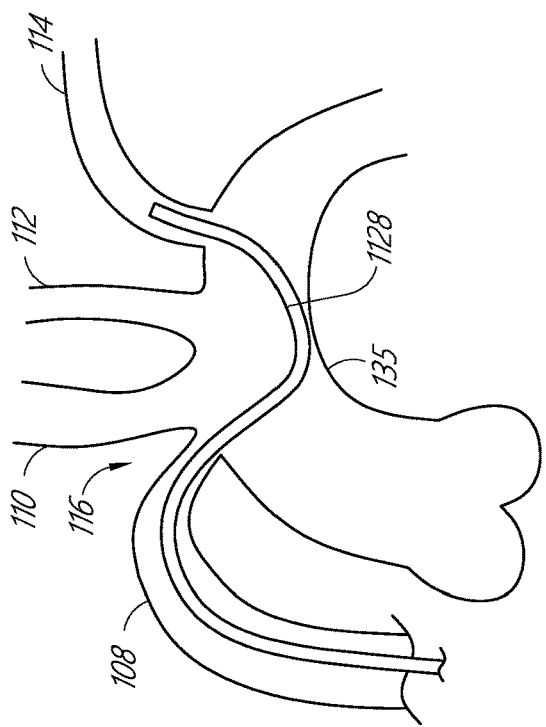

FIGS. 11G-11J schematically illustrate the delivery sequence for the protection system 1100. In FIG. 11G, the filter wire 1125 is loaded into the filter sheath 1127 and into the configuration shown in FIG. 11H. The first filter assembly 1102 is shown in its deployed configuration in FIG. 11I and its collapsed configuration in FIG. 11J. A guidewire 1123 can be loaded into the first filter assembly 1102. FIG. 11K illustrates the right radial access point 1103 and the target location 1105.

Figure 11L:
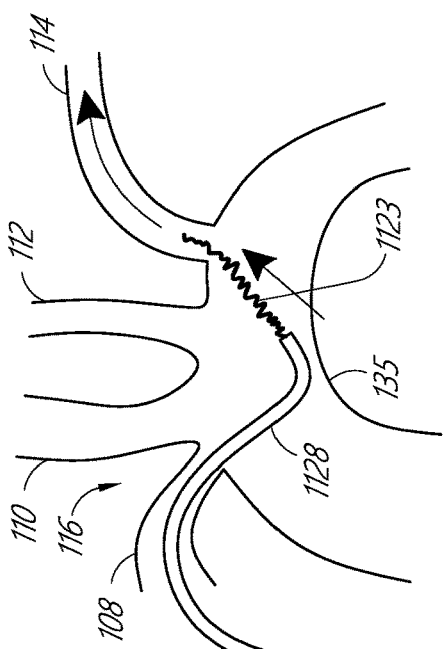
Figure 11L:
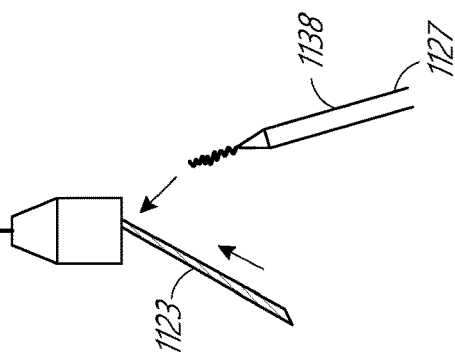
Figure 11N:
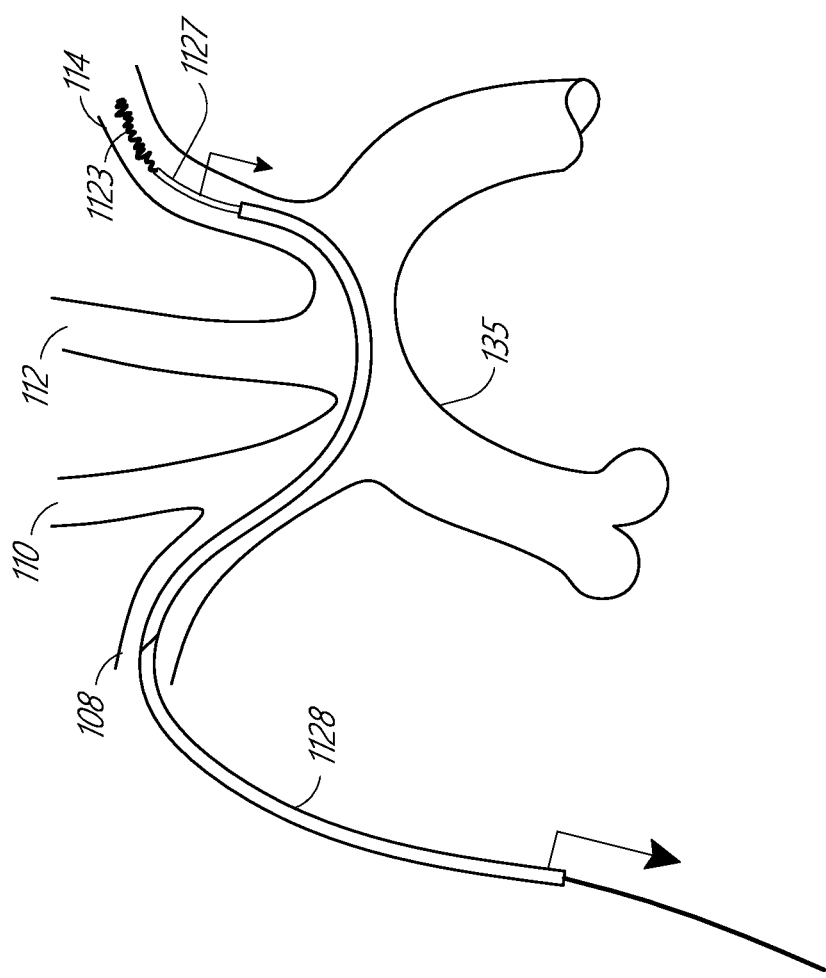
Figure 11O:
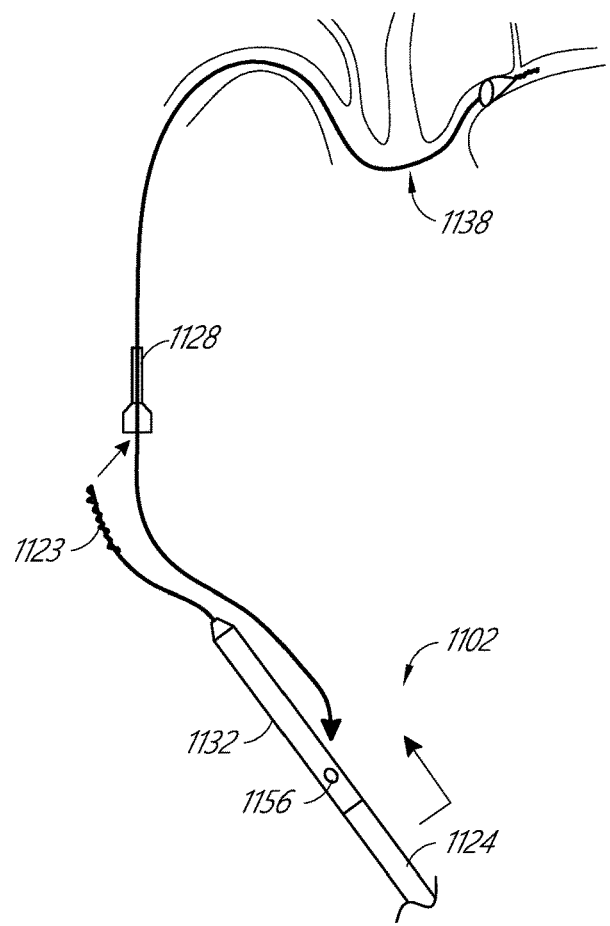
Figure 11P:
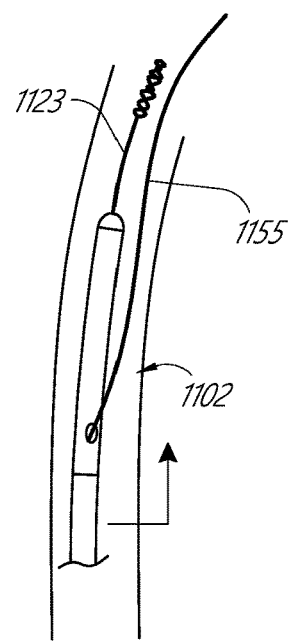
Figure 11Q:
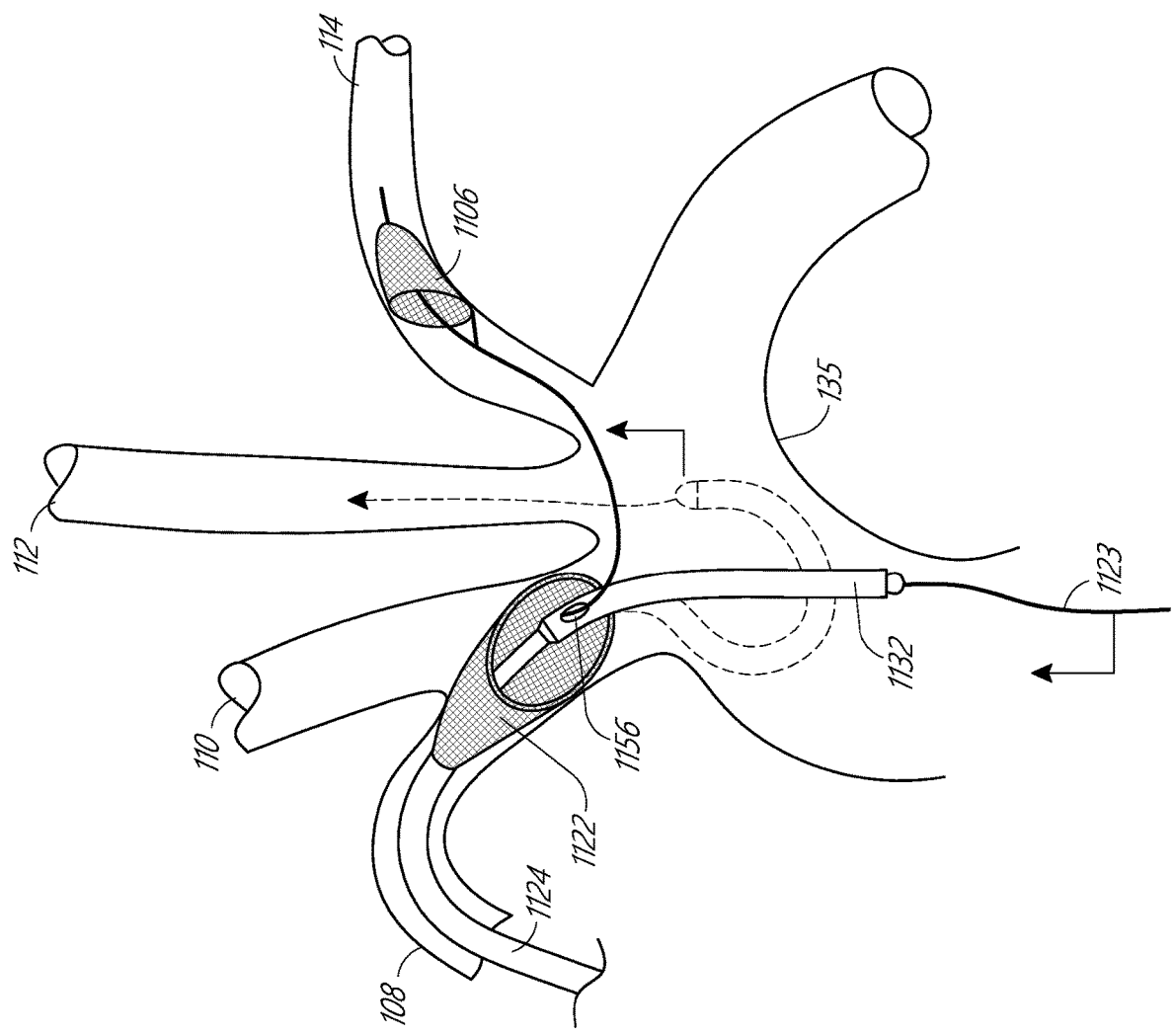
Figure 11S:
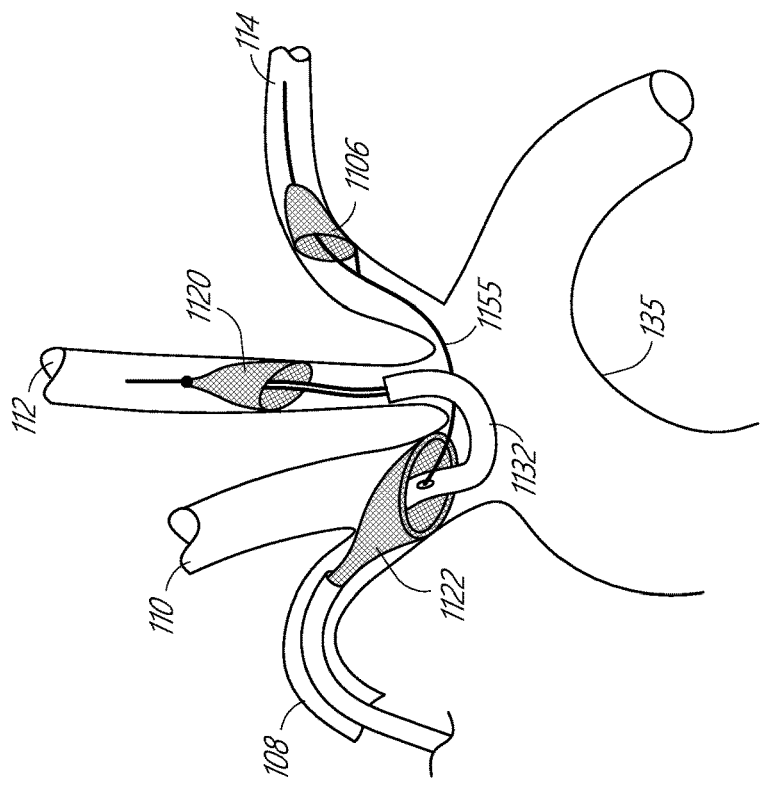
Figure 11R:
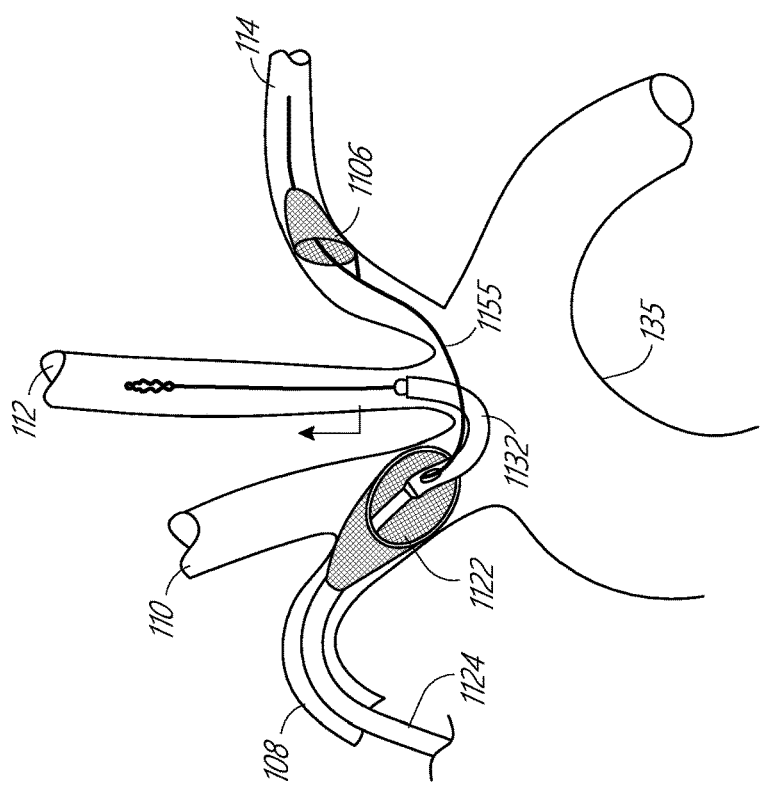

FIGS. 11L-11S illustrates a method of deploying the protection system 1100. The left subclavian artery 114 can be first accessed with an access catheter 1128 over a guidewire 1123 (FIG. 11L). The guidewire 1123 can be removed (FIG. 11M) and the accessory filter assembly 1138 can be inserted through the access catheter 1128. Alternatively, the accessory filter assembly 1138 can be inserted without the filter sheath 1127. The accessory filter sheath 1127 can be retracted to deploy the filter 1106 (FIG. 11N) or the distal filter 1106 can be advanced distally of the filter sheath 1127. The guide catheter 1128 and the accessory filter sheath 1127 can then be removed, leaving the accessory filter assembly 1138 in place. The accessory filter assembly 1138 can then be loaded into the dual filter assembly 1102 as shown in FIGS. 11O-11P with the filter wire 1125 entering a guidewire entry port 1156. The dual filter assembly 1102 can be loaded over an independent guidewire 1123. The dual filter assembly 1102 can be advanced over the independent guidewire 1123. A proximal filter 1122 can be deployed in the brachiocephalic trunk 134 (FIG. 11Q). After the proximal filter 1122 has been deployed, the independent guidewire 1123 can be retracted, the articulating sheath 1132 can be deflected, and the left common carotid artery 1112 can be cannulated with the guidewire 1123. The dual filter assembly 1102 can be pulled back so articulating distal sheath 1132 rests against the vessel carina (FIG. 11R). A secondary distal filter 1120 can be placed in the left common carotid artery 112, as shown in FIG. 11S.

TERMINOLOGY

Although certain filter assemblies have been described or illustrated herein as including a filter, the filters described herein can also be a self-expanding stent, a balloon, a deflector, or other occluding device.

Although certain filter assemblies have been described or illustrated herein as being introduced through a right radial or right brachial artery, the filter assemblies may alternatively be introduced through a left radial or left brachial artery. Similarly, although certain filter assemblies have been described or illustrated herein as being introduced through a left radial or left brachial artery, the filter assemblies may alternatively be introduced through a right radial or right brachial artery.

As used herein, the relative terms "proximal" and "distal" shall be defined from the perspective of the protection system. Thus, proximal refers to the direction of the handle portion of the delivery system and distal refers to the direction of the distal tip.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, or within less than 0.01% of the stated amount.

Although certain embodiments and examples have been described herein, it may be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art may recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The methods disclosed herein may include certain actions taken by a practitioner; however, the methods can also include any third-party instruction of those actions, either expressly or by implication. For example, actions such as "advancing a first filter assembly" includes "instructing advancing a first filter assembly."

What is claimed:

1. A protection system for preventing embolic material from entering cerebral vasculature, the protection system comprising:
    an outer sheath;
    an articulatable distal sheath positioned radially inward of the outer sheath;
    a distal filter, the distal filter configured to be deployed in a first vessel;
    a proximal filter disposed proximate a distal end of the outer sheath and configured to be deployed within a third vessel; and
    a debris deflector positioned between the proximal filter and the articulatable distal sheath in a pre-deployment configuration, the debris deflector configured to seal against an ostium of a second vessel,
    wherein in a post-deployment configuration, the distal filter is positioned distal to the debris deflector.

2. The protection system of claim 1, wherein the debris deflector comprises an opening, the articulatable distal sheath configured to be advanced through the opening of the debris deflector.

3. The protection system of claim 1, wherein the distal filter is distinct and separate from the debris deflector.

4. The protection system of claim 1, wherein the first vessel is a left subclavian artery.

5. The protection system of claim 1, wherein the second vessel is a left common carotid artery.

6. The protection system of claim 1, wherein the third vessel is a brachiocephalic artery.

7. The protection system of claim 1, wherein the distal filter is open at a proximal end thereof and closed at a distal end thereof.

8. The protection system of claim 1, wherein the proximal filter is open at a distal end thereof.

9. The protection system of claim 1, wherein the debris deflector is configured to conform to a wall of an aorta in a vicinity of the ostium of the second vessel.

10. The protection system of claim 9, wherein a central portion of the debris deflector includes a dome-shaped portion sized and configured to seal against a wall of a left common carotid artery proximate the ostium thereof.

11. The protection system of claim 1, wherein the articulatable distal sheath is sized and adapted to releasably contain the distal filter prior to delivery of the distal filter at least partially within the first vessel.

12. The protection system of claim 1, wherein the debris deflector can be rotated, translated, and/or apposed to an aortic arch by pulling against either the articulatable distal sheath or a deployed distal filter.

13. A protection system for preventing embolic material from entering cerebral vasculature, the protection system comprising:
- an outer sheath;
- an articulatable distal sheath positioned radially inward of the outer sheath;
- a distal filter having a first compressed configuration sized to be received at least partially within a distal portion of the articulatable distal sheath and a second post deployment configuration sized and configured to be received within a left subclavian artery;
- a debris deflector configured to conform to a wall of an aorta in a vicinity of an ostium of a left common carotid artery to seal against the ostium; and
- a proximal filter disposed proximate a distal end of the outer sheath and configured to be received within a brachiocephalic artery in a deployed configuration.

14. The protection system of claim 13, wherein the distal filter is open at a proximal end thereof and closed at a distal end thereof.

15. The protection system of claim 13, wherein the proximal filter is open at a distal end thereof.

16. The protection system of claim 13, wherein a central portion of the debris deflector includes a dome-shaped portion sized and configured to seal against a wall of left common carotid artery proximate the ostium thereof.

17. The protection system of claim 13, wherein the articulatable distal sheath is sized and adapted to releasably contain the distal filter prior to delivery of the distal filter at least partially within the brachiocephalic artery.

18. A method of delivering and deploying a protection system for preventing embolic material from entering cerebral vasculature, the method comprising:
- advancing an outer sheath that contains a distal filter, an articulatable distal sheath, a debris deflector, and a proximal filter, each in a compressed configuration, through a right subclavian artery of a patient to position a distal end of the outer sheath within a brachiocephalic artery;
- extending the articulatable distal sheath containing the distal filter from the outer sheath;
- articulating the articulatable distal sheath to position a distal end of the articulatable distal sheath adjacent to an ostium of a left subclavian artery of the patient;
- extending the distal filter from the articulatable distal sheath to within the left subclavian artery of the patient and expanding the distal filter within the left subclavian artery to seal a proximal mouth of the distal filter against a wall of the left subclavian artery;
- deploying the debris deflector with an aorta of the patient in apposition to the wall of the aorta at the ostium of a left common carotid artery; and
- expanding the proximal filter with the brachiocephalic artery to seal a distal mouth of the proximal filter against the wall of the brachiocephalic artery,
- wherein in their respective deployed configurations the mouth of the distal filter and the mouth of the proximal filter each face the debris deflector.

19. The method of claim 18, wherein a proximal end of the proximal filter is affixed to the distal end of a core shaft disposed within the outer sheath.

20. The method of claim 18, further comprising performing a transcatheter heart procedure.

* * * * *